United States Patent [19]

Gearing et al.

[11] Patent Number: 5,427,925
[45] Date of Patent: * Jun. 27, 1995

[54] RECOMBNIANT METHOD FOR MAKING LEUKEMIA INHIBITOR FACTOR

[75] Inventors: David P. Gearing, North Fitzroy; Nicholas M. Gough, North Balwn; Douglas J. Hilton, Warrandyte; Julie A. King, Nunawading; Donald Metcalf, Balwyn; Edouard C. Nice, St. Kilda; Nicos A. Nicola, Regent; Richard J. Simpson, Richmond; Tracy A. Willson, North Balwyn, all of Australia

[73] Assignee: Amrad Corporation Limited, Victoria, Australia

[ * ] Notice: The portion of the term of this patent subsequent to Feb. 16, 2010 has been disclaimed.

[21] Appl. No.: 58,979

[22] Filed: May 6, 1993

Related U.S. Application Data

[60] Continuation of Ser. No. 948,614, Sep. 22, 1992, which is a continuation of Ser. No. 667,159, Mar. 11, 1991, abandoned, which is a division of Ser. No. 294,514, Dec. 9, 1988, Pat. No. 5,187,077.

[30] Foreign Application Priority Data

| Apr. 2, 1987 | [AU] | Australia | PI2109 |
| Jul. 24, 1987 | [AU] | Australia | PI3317 |
| Oct. 15, 1987 | [AU] | Australia | PI4903 |
| Dec. 21, 1987 | [AU] | Australia | PI6005 |

[51] Int. Cl.⁶ ............... C12N 15/19; C12N 1/21; C12N 5/10; C12N 15/85
[52] U.S. Cl. ................. 435/69.5; 435/69.8; 435/240.2; 435/252.33
[58] Field of Search ........... 435/69.5, 69.1, 69.8, 435/240.2, 252.33, 255; 530/351, 395

[56] References Cited

U.S. PATENT DOCUMENTS

| 4,578,355 | 3/1986 | Rosenberg | 435/172.3 |
| 4,616,079 | 10/1986 | Gottlieb | 530/380 |
| 4,760,021 | 7/1988 | Mimura et al. | 435/351 |
| 5,187,077 | 2/1993 | Gearing et al. | 435/69.1 |

FOREIGN PATENT DOCUMENTS

| 66756 | 3/1986 | Australia |
| 1-148197 | 6/1989 | Japan |

OTHER PUBLICATIONS

Fukada, "Purification and Partial Characterization of a Cholinergic Neuronal Differentiation Factor", *PNAS* 82: 8795–8799 (Dec. 1985).

Yamamori et al, "The Cholinergic Neuronal Differentiation Factor . . . is Identical to Leukemia Inhibitory Factor", *Science* 246: 1412–1416 (Dec. 1989).

Koopman et al, "A Factor . . . Which Inhibits . . . Cell Differentiation", *Exp. Cell Res.* 154: 233–242 (Sep. 1984).

Williams et al, "Myeloid Leukaemia Inhibitory Factor . . . " *Nature* 336: 684–678 (Dec. 1988).

Wong et al "Human GM-CSF . . . Purification of the Natural and Recombinant Proteins", *Science* 228: 810–815 (May 1985).

Lathe, "Synthetic Oligonucleotide Probes . . . " *J. Mol. Biol.* 183: 1–12 (1985).

Huynh et al, pp. 49–78 in *DNA Cloning*, vol. 1, edited by Glover, (1985).

Ernst, "Improved Secretion of Heterologous Proteins . . . " *DNA* 5: 483–491 (1986).

Moreau et al, *Biol. Abst.* 81(12): AB-89, Ref No. 112012 (Jun. 1986).

Moreau et al, "Leukaemia Inhibitory Factor is Identical to the Myeloid Growth Factor . . . ", *Nature* 336: 690–692, (Dec. 1988).

(List continued on next page.)

*Primary Examiner*—Stephen G. Walsh
*Attorney, Agent, or Firm*—Scully, Scott, Murphy & Presser

[57] ABSTRACT

The present invention provides a method for producing recombinant leukemia inhibitory factor (LIF) by the expression, in suitable host cells, of recombinant DNA molecules encoding LIF.

22 Claims, 35 Drawing Sheets

OTHER PUBLICATIONS

Moreau et al, "Characterization of a Factor . . . " *J. Immunol.* 138: 3844–3849 (Jun. 1987).

Potter et al, "Enhancer–Dependent Expression . . . " *PNAS* 81: 7161–7165 (Nov. 1984).

Shabo et al "The Myeloid Blood Cell Differentiation–Inducing Protein MGI-2A Is Interleaukin-6", *Blood* 72(6): 2070–2073 (Dec. 1988).

Weber et al, "A Diffusible Factor Responsible for the Determination of Cholinergic Functions . . . ", *J. Biol. Chem.* 256(7): 3447–3453 (Apr. 1981).

Fukada et al "Hormonal Control of Neurotransmitters Choice . . . " *Nature* 287: 553–555 (Oct. 1980).

Tomida et al., J. Biol. Chem. 259: 10978–10982 (1984).

Tomida et al., FEBS Letters 178: 291–296 (1984).

Lowe et al., DNA 8: 351–359 (1989).

Abe et al., Proc. Natl. Acad. Scie. 83: 5958–5962 (1986).

Hilton et al., J. Cell. Biochem, 46: 21–26 (1991).

Gearing et al. "Cloning, Sequencing, and Expression of Murine and Human Leukemia Inhibitory Factor (LIF—)-encoding DNA" CA110: 187328 t (1989).

Sachs, J. Cell. Physiol, Supp. 1:151–164 (1982).

Lipton and Sachs, Biochem. Biophys. Acta, 673:552–569 (1981).

Nicola, et al., J. Biol. Chem. 258:9017–9023 (1983).

Takeda, et al., Nature 323–338–340 (1986).

Nicola and Metcalf, J. Cell. Physiol., 128–180–188 (1986).

Kelso, et al., J. Immunol., 136:1718–1725 (1986).

Grantham, et al., Nucleic Acids Res., 9:r43–r74 (1981).

Kelso, et al., Exp. Hematol., 13:7–15 (1985).

Gough, J. Mol. Biol., 165:683–699 (1983).

Gearing, et al., Embo J., 6:3995–4002 (1987).

Smith and Johnson, Gene, 67:31–40 (1988).

Baumann, H., Hill, R. E., Sauder, D. N. and Jahreis, G. P. (1986), J. Cell Biol. 102(2) pp. 370–383.

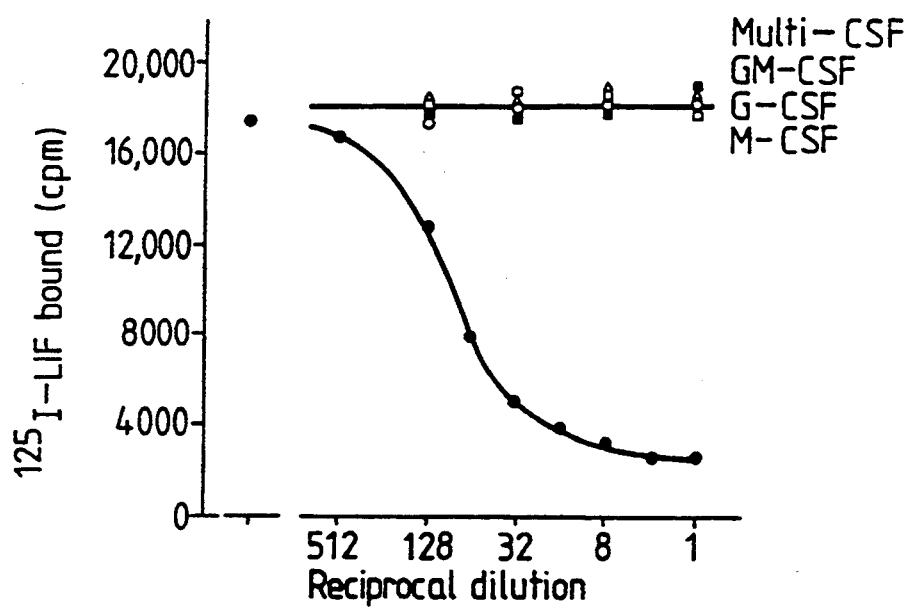
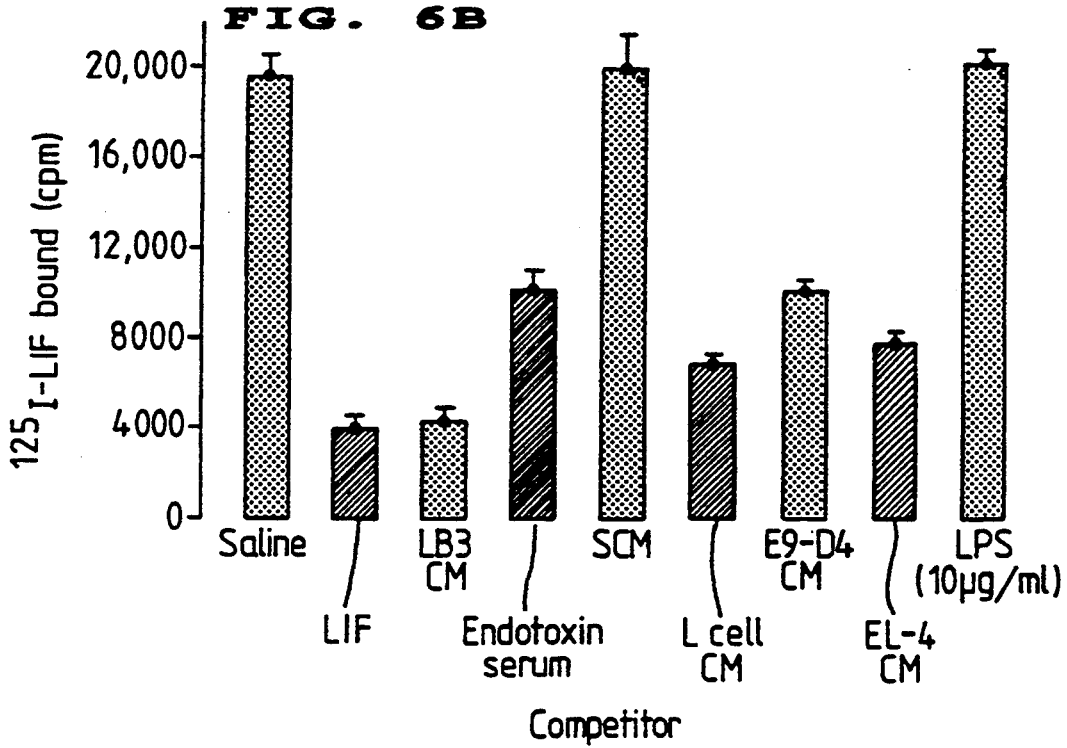

```
       15
       HisProCysHisGlyAsnLeuMetAsnGlnIleLys           LIF

CUN        A
5' CACCCNUGCCACGGNAACUUAAUGAACCAAAUCAAA 3'   LIF mRNA
       U    U  U     U  G    U G U G

3' GTGGGGACGGTACCATTGGAGTACTTGGTCTAGTT 5'    LIF OLIGO
       A    A     G     C         A
```

```
                    ###              ###         * * *
HisTrpLysHisGlyAlaGlySerProLeuProIleThrProValAsnAl      17
CACTGGAAACACGGGGCAGGGAGCCCTCTTCCCATCACCCCTGTAAATGC      50 aThrCysAlaIleArgHisProCysHisGlyAsnLeuMetAsnGlnIleL      34
CACCTGTGCCATACGCCACCCATGCCACGGCAACCTCATGAACCAGATCA     100
                * * *
ysAsnGlnLeuAlaGlnLeuAsnGlySerAlaAsnAlaLeuPheIleSer      50
AGAATCAACTGGCACAGCTCAATGGCAGCGCCAATGCTCTCTTCATTTCC     150

TyrTyrThrAlaGlnGlyGluProPheProAsnAsnValGluLysLeuCy      67
TATTACACAGCTCAAGGAGAGCCGTTTCCCAACAACGTGGAAAAGCTATG     200
       * * *    ###                          * * *
sAlaProAsnMetThrAspPheProSerPheHisGlyAsnGlyThrGluL      84
TGCGCCTAACATGACAGACTTCCCATCTTTCCATGGCAACGGGACAGAGA     250 ysThrLysLeuValGluLeuTyrArgMetValAlaTyrLeuSerAlaSer     100
AGACCAAGTTGGTGGAGCTGTATCGGATGGTCGCATACCTGAGCGCCTCC     300
      * * *                     * * *      ###
LeuThrAsnIleThrArgAspGlnLysValLeuAsnProThrAlaValSe     117
CTGACCAATATCACCCGGGACCAGAAGGTCCTGAACCCCACTGCCGTGAG     350
                     * * *
rLeuGlnValLysLeuAsnAlaThrIleAspValMetArgGlyLeuLeuS     134
CCTCCAGGTCAAGCTCAATGCTACTATAGACGTCATGAGGGGCCTCCTCA     400 erAsnValLeuCysArgLeuCysAsnLysTyrArgValGlyHisValAsp     150
GCAATGTGCTTTGCCGTCTGTGCAACAAGTACCGTGTGGGCCACGTGGAT     450

ValProProValProAspHisSerAspLysGluAlaPheGlnArgLysLy     167
GTGCCACCTGTCCCCGACCACTCTGACAAAGAAGCCTTCCAAAGGAAAAA     500 sLeuGlyCysGlnLeuLeuGlyThrTyrLysGln                   178
GTTGGGTTGCCAGCTTCTGGGGACATACAAGCAAG                  535
```

A  F  Q  R  K  K  L  G  C──Q  L  L  G  T  Y  K
GCCTTCCAAAGGAAAAAGTTGGGTTGCCAGCTTCTGGGGACATACAAG
```

```
                      187
Q                                              pLIF7.2b cDNA

Q  V  I  S  V  V  V  Q  A  F                  V8 peptide

Q  V  I  S  V  V  X  Q  A  F                  Tryptic peptide

Q  V  I  S  V  V  V  Q  A  F  *                pLIFNK1 cDNA
CAAGTCATAAGTGTGGTGGTCCAGGCCTTCTAG
```

*Fig. II.*

```
                              5                              178
                    ----GlyAlaGlySerProLeu            LysGln
pLIF7.2b       5'   ----GGGGCAGGGAGCCCTCTT--------AAGCAAG

GlySerProLeu--------LysGln*
                         GGATCCCCTCTT--------AAGCAAT
pLIFmut1
                         ------

GlySerProLeu--------LysGlnV
pLIFmut2                 GGATCCCCTCTT--------AAGCAAG
                         ------

YEpsec leader ----GlnGlyThrArgGlySer
                    CAAGGTACCCGGGGATCC
                                ------
                              Bam HI
```

```
 3'
 *****
AATAGATATCAAGCTT
 alIleSerValValValGlnAlaPhe******
 TGATCAGCGTGGTGGTGCAGGCCTTCTAATAGATATCAAGCTTAGCTCGAATTC
                                         ------   ------
                                         Hind 3   Eco RI
```

FIG.12.

```
         EcoRI                    MetLysValLeuAlaAlaGlyIleValP
         GAATTCCGGAGTCCAGCCCATAATGAAGGTCTTGGCCGCAGGGATTGTGC          50
         ------                                        +1
         roLeuLeuLeuLeuValLeuHisTrpLysHisGlyAlaGlySerProLeu
         CCTTACTGCTGCTGGTTCTGCACTGGAAACACGGGGCAGGGAGCCCTCTT         100

ProIleThrProValAsnAlaThrCysAlaIleArgHisProCysHisGl
         CCCATCACCCCTGTAAATGCCACCTGTGCCATACGCCACCCATGCCACGG         150 yAsnLeuMetAsnGlnIleLysAsnGlnLeuAlaGlnLeuAsnGlySerA
         CAACCTCATGAACCAGATCAAGAATCAACTGGCACAGCTCAATGGCAGCG         200 laAsnAlaLeuPheIleSerTyrTyrThrAlaGlnGlyGluProPhePro
         CCAATGCTCTCTTCATTTCCTATTACACAGCTCAAGGAGAGCCGTTTCCC         250

AsnAsnValGluLysLeuCysAlaProAsnMetThrAspPheProSerPh
         AACAACGTGGAAAAGCTATGTGCGCCTAACATGACAGACTTCCCATCTTT         300 eHisGlyAsnGlyThrGluLysThrLysLeuValGluLeuTyrArgMetV
         CCATGGCAACGGGACAGAGAAGACCAAGTTGGTGGAGCTGTATCGGATGG         350 alAlaTyrLeuSerAlaSerLeuThrAsnIleThrArgAspGlnLysVal
         TCGCATACCTGAGCGCCTCCCTGACCAATATCACCCGGGACCAGAAGGTC         400

LeuAsnProThrAlaValSerLeuGlnValLysLeuAsnAlaThrIleAs
         CTGAACCCCACTGCCGTGAGCCTCCAGGTCAAGCTCAATGCTACTATAGA         450 pValMetArgGlyLeuLeuSerAsnValLeuCysArgLeuCysAsnLysT
         CGTCATGAGGGGCCTCCTCAGCAATGT-CTTTGCCGTCTGTGCAACAAGT         500 yrArgValGlyHisValAspValProProValProAspHisSerAspLys
         ACCGTGTGGGCCACGTGGATGTGCCACCTGTCCCCGACCACTCTGACAAA         550
```

FIG. 15A.

```
            GluAlaPheGlnArgLysLysLeuGlyCysGlnLeuLeuGlyThrTyrLy
            GAAGCCTTCCAAAGGAAAAAGTTGGGTTGCCAGCTTCTGGGGACATACAA  600 sGlnValIleSerValValValGlnAlaPhe***
            GCAAGTCATAAGTGTGGTGGTCCAGGCCTTCTAGAGAGGAGGTCTTGAAT  650
                                          ------
                                           xba I
            GTACCATGGACTGAGGGACCTCAGGAGCAGGATCCGGAGGTGGGGAGGGG  700
            GCTCAAAATGTGCTGGGGTTTGGGACATTGTTAAATGCAAAACGGGGCTG  750
            CTGGCAGACCCCAGGGATTTCCAGGTACTCACTGCACTCTGGGCTGGGCC  800
            ATGATGGAATCTGGCAAAGTTGAAACTTCCATAGGCAGAGCTTCTATACA  850
            GCCCAGCACCAGCTAGAAATGGCAATGAGGGTGTTGGTCTGAGAGATTTC  900
            TGTCTCACTCACTCACTCACTCTCACTCACTCACTCACTCACTCACTCAC  950
            TCAGCCCCTTGCTTGCTGGGTGTAGAACAAGCTGCCACAAGTTGTCTACA 1000
            GCAGACAGCAAAGGGCTGGGAAGTGTCCTAGACCCCTACAGAGTCACCAT 1050
            CATCTGGTCCTTTGCTGTCTCTCAGAGAAACTTTGGAAGGCTTGGTTGGG 1100
            ATGTGAGAGAGCTAAGGGGACTGGGATCCAGAAGGAATCCTTTTATTTTA 1150
            TTTTATTTTATTTTATTTTATTTTATAAGTTTTGTGGGTGGAAGG      1200
            GTACCCTGGGGTGGAATGATGGAATGTGTCTTCTCTTGAGTTGGATGAGA 1250
            GAGTTCAGGCTTAGAGACTGTCAGATGGAAGAGTCTACCTCACCAGTGTT 1300
            CAGCTCCCACAGAAGCACAGCGGCCAGCTTCCAGTTGTCAAAGCCT-ACG 1350
            AACTCGGTTAGCTTCTATGCAGTTCCCCCCACAGCCTGGCGTGGTTGGGG 1400
            TCTGCCAGCTGGACCTAGAGGTGAGGTGTGTGGAATTC             1438
```

*FIG. 15B.*

```
              Glutathione
              S-transferase    Thrombin                     M-LIF
              ---------------  _____          ............
         N -----Pro Lys Ser Asp Leu Val Pro Arg Gly Ser Pro Leu Pro Ile-----C
         5'-----CCA AAA TCG GAT CTG GTT CCG CGT GGA TCC CCT CTT CCC ATC-----3'
                                                 -------
                                                  Bam HI
```

(a) 5'-CTGCACTGGACCTTAGGGGCGGGATCCCCCCTCCCCATC-3'
                                  ------
                                  Bam HI (b) 5'-GCCAATGCCCTCTTTATTCTCTATTACACAGCCCAGGGGGAGCCGTTC-3'

(c) 5'-CAGGCCTTCTAGTAAGATATCAAGCTTTGTGCTGTGAAC-3'
                                 ------
                                 Hind 3

6 x SSC 65°C

```
              GlyValValProLeuLeuLeu---Val
H  TCCCCAGGAGTTGTGCCCTGCTGTTG---GTT
      **  ********  *  ***  **    ***
M        gggattgtgcccttactgctggtt rgHisProCysHisAsnAsnLeuMetAsnGlnI
H  GCCACCCATGTCACAACAACCTCATGAACCAGA
   *********  ***  ****************
M  gccacccatgccacggcaacctcatgaaccaga H  CTGGGATACTGACAGGAGATGGCAGGGAGGGGG
H  ATGGGGAGAGGGCTTGATTAAACCACCCCCAGA
H  AACTGAGTGCAAAGGTGGGGACCTGGCACTTCT
H  ATGCGGTTGAGAGGCAGTGGGCTGTGGGTGCTG
H  TAGGGCTAGACACCGAGTTTTCCCTTCTGTCCC
H  GCAAGGGCACTCACATTACAATTAGTTTTGGCT

H  CGCAAGAGCTTGCCCAAAGGGTTGGCGGCAGGG

M

ProPheProAsnAsnLeuAspLysLeuCysGly
H  CCGTTCCCCAACAACCTGGACAAGCTATGTGGC
   *****  *********  ****  *********
M  ccgtttcccaacaacgtggaaaagctatgtgcg yrArgIleValValTyrLeuGlyThrSerLeuG
H  ACCGCATAGTCGTGTACCTTGGCACCTCCCTGG
   *  **  **  ****    *****  ********
M  atcggatggtcgcatacctgagcgcctccctga aThrAlaAspIleLeuArgGlyLeuLeuSerAs
H  CACCGCCGACATCCTGCGAGGCCTCCTTAGCAA
   **     ***  **  **  *  ********  *****
M  tactatagacgtcatgaggggcctcctcagcaa SerGlyLysAspValPheGlnLysLysLysLeu
H  TCGGGTAAGGATGTCTTCCAGAAGAAGAAGCTG
   *  *    **  **  *  ******  *  ***  ***  **
M  tctgacaaagaagccttccaaaggaaaaagttg
```

LeuHisTrpLysHisGlyAlaGlySerProLeuPro
CTGCACTGGAAACATGGGGCGGGGAGCCCCCTCCCC
************ * ****  ***
ctgcactggaaacacggggcagggagccctcttccc leArgSerGlnLeuAlaGlnLeuAsnGlySerAlaA
TCAGGAGCCAACTGGCACAGCTCAATGGCAGTGCCA
*  ******************* **
tcaagaatcaactggcacagctcaatggcagcgcca CTTGTAAATATCATTAGGGGCTGTCCTGATCTGGGT
CTCCTGCCACTTCCTGCCAAGCTTCCCCAGGGAAG
TATCTTGTGATTGTCCTGCTGCAGGGAGCGAGGGAT
GGCATGGAGGGGCGTCCCGGAACATTGTGAGTGCAG
CTTAGGGTGGTGATGATGATGATGATGATAATGATG
CTCATGACAATTCCAGATGCTTACAGGGCAAGGAGT

CTGGGACACTGACCCCTGACTCCCACGTCACCTCCC

ProAsnValThrAspPheProProPheHisAlaAsn
CCCAACGTGACGGACTTCCCGCCCTTCCACGCCAAC
 * ** ***** * ***** * ****
cctaacatgacagacttcccatctttccatggcaac lyAsnIleThrArgAspGlnLysIleLeuAsnProS
GCAACATCACCCGGGACCAGAAGATCCTCAACCCCA
* *************  *****
ccaatatcacccgggaccagaaggtcctgaacccca nValLeuCysArgLeuCysSerLysTyrHisValGl
CGTGCTGTGCCGCCTGTGCAGCAAGTACCACGTGGG
***  *** **** ***
tgtgctttgccgtctgtgcaacaagtaccgtgtggg GlyCysGlnLeuLeuGlyLysTyrLysGlnIleIle
GGCTGTCAACTCCTGGGGAAGTATAAGCAGATCATC
    *****  *** **
ggttgccagcttctggggacatacaagcaagtcata

FIG.25B.

```
          IleThrProValAsnAlaThrCysAlaIleA
          ATCACCCCTGTCAACGCCACCTGTGCCATAC        97
          ********** ** *****************
          atcacccctgtaaatgccacctgtgccatac snAlaLeuPheIleLeuTyr
          ATGCCCTCTTTATTCTCTATGTAAGTTACCC       197
          **** ***** ***    ****
          atgctctcttcatttcctat TGAGGGGACCTTTTGGGGCTGGAAGGAGAGA       297
          CTTCCCCAGGGTGCCCAGTTAGCAAGGGGAG       397
          GGAGGGGAAATGGGCGTGAGGCACCAGGGAG       497
          GGATGGAAGTACTTGTGTGTGGTGCCCCAGC       597
          ACTGCGTGCATGGCTCAGTCTTTGATCTTTA       697
          TGGGTCCTCATGCGCTAGATGGGGAAACAGA       797

TyrThrAlaGlnGlyGlu
          TTCTGCCCCTCAGTACACAGCCCAGGGGGAG       897
                   ******** ** ** ***
                   tacacagctcaaggagag GlyThrGluLysAlaLysLeuValGluLeuT
          GGCACGGAGAAGGCCAAGCTGGTGGAGCTGT       997
          ** ** ****** ***** ************
          gggacagagaagaccaagttggtggagctgt erAlaLeuSerLeuHisSerLysLeuAsnAl
          GTGCCCTCAGCCTCCACAGCAAGCTCAACGC      1097
          **** * ********   ********* **
          ctgccgtgagcctccaggtcaagctcaatgc yHisValAspValThrTyrGlyProAspThr
          CCATGTGGACGTGACCTACGGCCCTGACACC      1197
          *** ***** *** *     * *** *** *
          ccacgtggatgtgccacctgtccccgaccac AlaValLeuAlaGlnAlaPheTER
          GCCGTGTTGGCCCAGGCCTTCTAGCAGGAGG      1297
              *** *** ************* ** ***
              agtgtggtggtccaggccttctag-ag-agg
```

FIG.25C.

```
M : ------------------------
H : ProLeuProIleThrProValAsnAla

M : -------------LysAsn------
H : LeuMetAsnGlnIle ArgSerGlnLeu

M : ---Ser-------------------
H : Ile LeuTyrTyrThrAlaGlnGlyGlu

M : ------Met-----------Ser---
H : ProAsnValThrAspPheProProPhe

M : -----------Met---Ala------
H : GluLeuTyrArgIleValValTyrLeu

M : ---Val---------Thr---Val---
H : LysIleLeuAsnProSerAlaLeuSer

M : Met----------------------
H : LeuArgGlyLeuLeuSerAsnValLeu

M : ---------ProProVal------His
H : ValAspValThrTyrGlyProAspThr

M : -----------------Thr------
H : GlyCysGlnLeuLeuGlyLysTyrLys
```

*FIG. 26A.*

```
-------------------------Gly---
ThrCysAlaIleArgHisProCysHisAsnAsn

---------------------------------
AlaGlnLeuAsnGlySerAlaAsnAlaLeuPhe

-------------ValGlu--------Ala-
ProPheProAsnAsnLeuAspLysLeuCysGly

---Gly-------------Thr---------
HisAlaAsnGlyThrGluLysAlaLysLeuVal

SerAla------Thr------------------
GlyThrSerLeuGlyAsnIleThrArgAspGln

---GlnVal--------------Ile---Val
LeuHisSerLysLeuAsnAlaThrAlaAspIle

------------Asn------Arg---------
CysArgLeuCysSerLysTyrHisValGlyHis

---Asp---GluAla------Arg--------
SerGlyLysAspValPheGlnLysLysLysLeu

---Val---Ser---ValVal---------
GlnIleIleAlaValLeuAlaGlnAlaPhe
```

FIG.26B.

```
                    +1
       GlySerProLeuProIleThrProValAsn
       GGATCCCCCTCCCCATCACCCCTGTCAAC
       ------
       BamHI

AsnAsnLeuMetAsnGlnIleArgSerGln
       AACAACCTCATGAACCAGATCAGGAGCCAA

LeuPheIleLeuTyrTyrThrAlaGlnGly
       CTCTTTATTCTCTATTACACAGCCCAGGGG

CysGlyProAsnValThrAspPheProPro
       TGTGGCCCCAACGTGACGGACTTCCCGCCC

LeuValGluLeuTyrArgIleValValTyr
       CTGGTGGAGCTGTACCGCATAGTCGTGTAC

AspGlnLysIleLeuAsnProSerAlaLeu
       GACCAGAAGATCCTCAACCCCAGTGCCCTC

AspIleLeuArgGlyLeuLeuSerAsnVal
       GACATCCTGCGAGGCCTCCTTAGCAACGTG

GlyHisValAspValThrTyrGlyProAsp
       GGCCATGTGGACGTGACCTACGGCCCTGAC

LysLeuGlyCysGlnLeuLeuGlyLysTyr
       AAGCTGGGCTGTCAACTCCTGGGGAAGTAT

Phe******
       TTCTAGTAAGATATCAAGCTT
                    ------
                    Hind3
```

*FIG. 29A.*

```
AlaThrCysAlaIleArgHisProCysHis
GCCACCTGTGCCATACGCCACCCATGTCAC    60

LeuAlaGlnLeuAsnGlySerAlaAsnAla
CTGGCACAGCTCAATGGCAGTGCCAATGCC   120

GluProPheProAsnAsnLeuAspLysLeu
GAGCCGTTCCCCAACAACCTGGACAAGCTA   180

PheHisAlaAsnGlyThrGluLysAlaLys
TTCCACGCCAACGGCACGGAGAAGGCCAAG   240

LeuGlyThrSerLeuGlyAsnIleThrArg
CTTGGCACCTCCCTGGGCAACATCACCCGG   300

SerLeuHisSerLysLeuAsnAlaThrAla
AGCCTCCACAGCAAGCTCAACGCCACCGCC   360

LeuCysArgLeuCysSerLysTyrHisVal
CTGTGCCGCCTGTGCAGCAAGTACCACGTG   420

ThrSerGlyLysAspValPheGlnLysLys
ACCTCGGGTAAGGATGTCTTCCAGAAGAAG   480

LysGlnIleIleAlaValLeuAlaGlnAla
AAGCAGATCATCGCCGTGTTGGCCCAGGCC   540

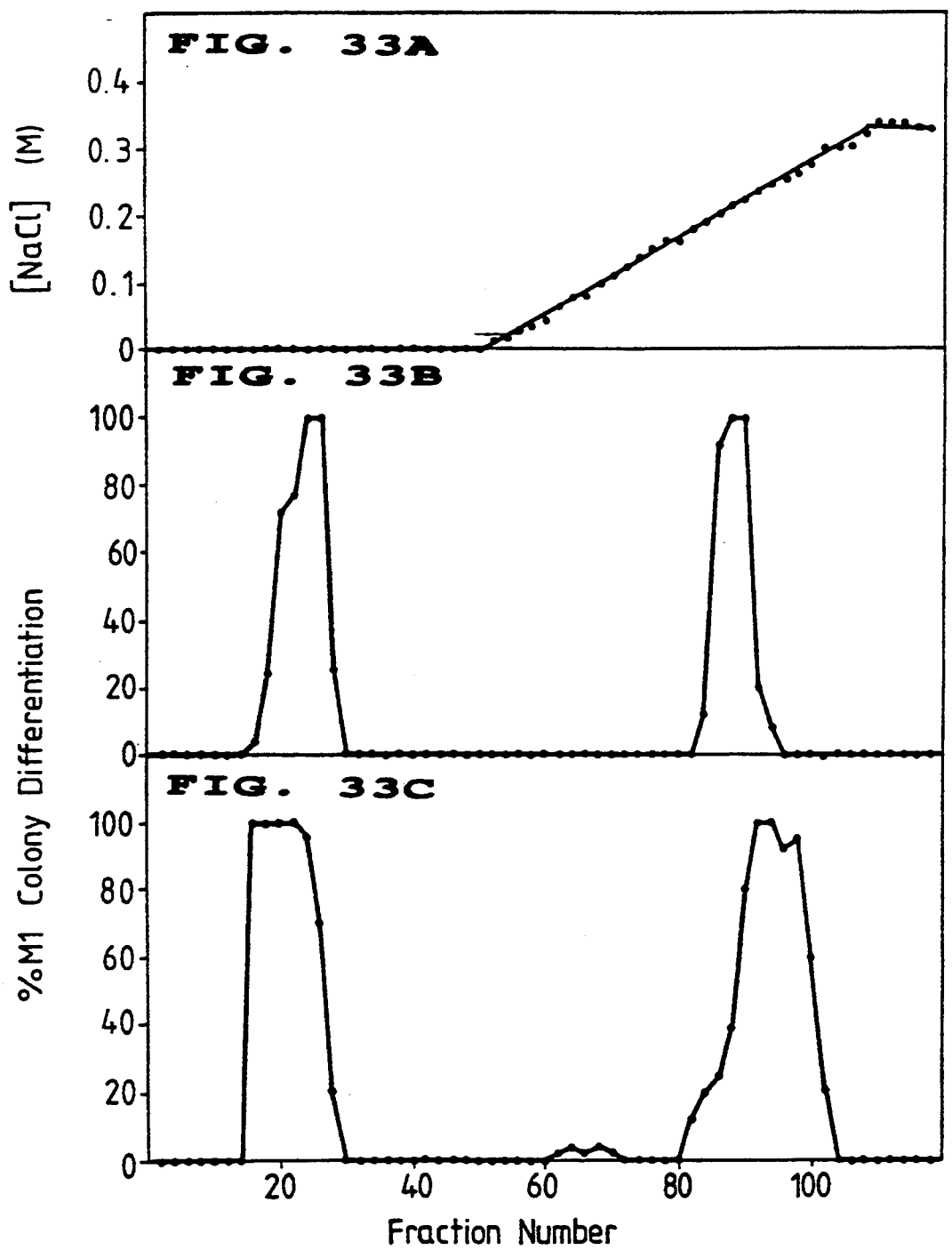

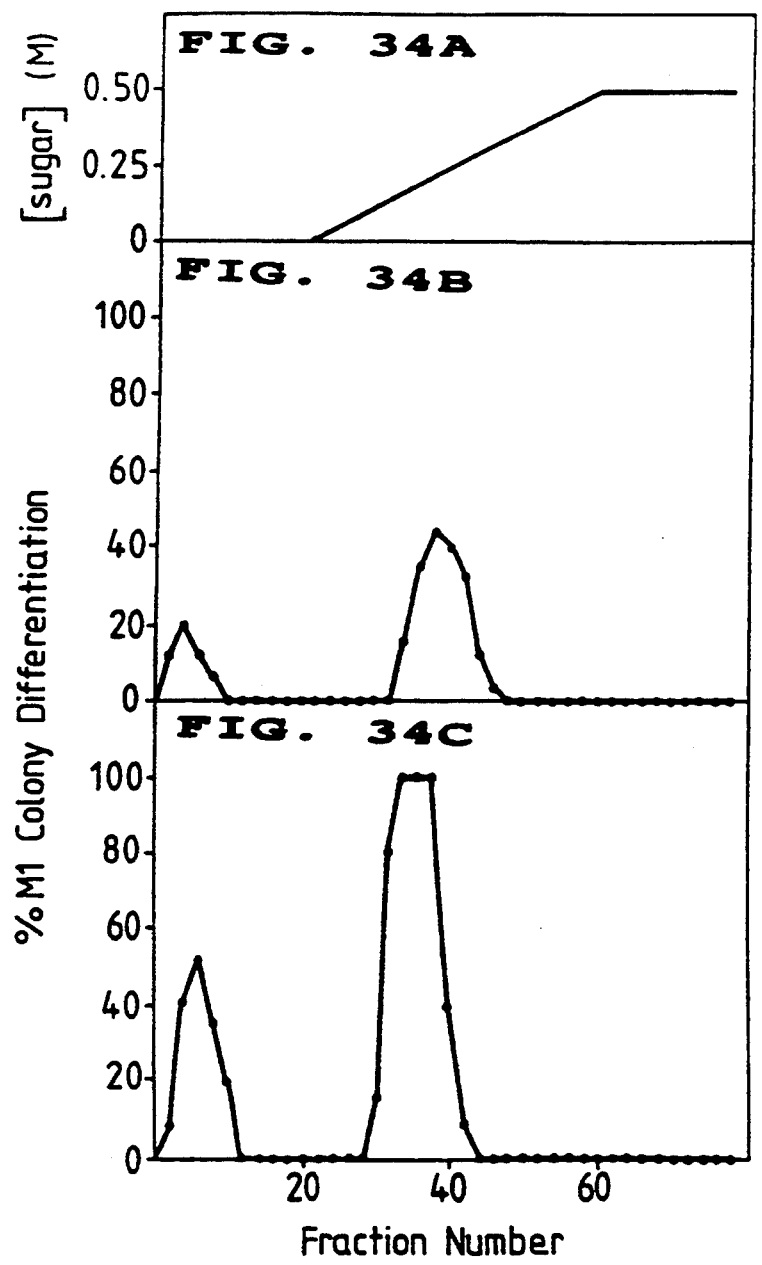

RECOMBNIANT METHOD FOR MAKING LEUKEMIA INHIBITOR FACTOR

This is a continuation of application Ser. No. 948,614, filed on Sep. 22, 1992, which is a continuation of Ser. No. 07/667,159 filed on Mar. 11, 1991, now abandoned, which is a divisional of Ser. No. 07/294,514 filed on Dec. 9, 1988, now U.S. Pat. No. 5,187,077, which is the national stage of International Application PCT/AU88/00093, filed on Mar. 31, 1988 and which designated the U.S.

FIELD OF THE INVENTION

This invention relates to Leukaemia Inhibitory Factor (LIF), to the production of LIF in substantially pure form, and to the cloning and expression of recombinant LIF.

BACKGROUND OF THE INVENTION

Mature blood cells are produced by the clonal proliferation and concomitant differentiation of immature precursor cells (Metcalf, D. (1984) *The Hemopoietic Colony Stimulating Factors,* Elsevier, Amsterdam.). For normal haemopoietic cells, the two processes of proliferation and differentiation are tightly coupled so that the short-lived mature cells are continually replenished. At least four biochemically distinct growth factors, the colony-stimulating factors (CSFs), have been shown in vitro to stimulate the proliferation and differentiation of precursor cells of granulocytes and macrophages: G-CSF, M-CSF, GM-CSF and Multi-CSF (IL-3) (see Metcalf, D. (1987), *Proc. R. Soc. B.* 230, 389–423, for review).

In contrast to normal cells, leukaemic myeloid cells are characterized by an uncoupling of proliferation and differentiation so that immature progenitor cells accumulate, retain their proliferative capacity and fail to differentiate. There has been considerable controversy concerning the nature of biological factors that are able to induce the differentiation of myeloid leukaemic cells in vitro and whether certain factors are capable of inducing differentiation in the absence of proliferation. Indeed, it has been proposed that the events of proliferation and differentiation are necessarily mediated by different factors (Sachs, L. (1982), *J. Cell. Physiol. Suppl.,* 1, 151–164). On the one hand, two groups have described and purified an activity (MGI-2 or D-factor) capable of inducing the differentiation of the murine myeloid leukaemic cell line M1, that does not stimulate the proliferation of normal progenitor cells (Lipton, J. H. and Sachs, L. (1981), *Biochem. Biophys. Acta.* 673, 552–569; Tomida, M., Yamamoto-Yamaguchi, Y., and Hozumi, M. (1984) *J. Biol. Chem.* 259, 10978–10982). On the other hand, the present inventors have previously shown that one of the CSFs, G-CSF, is a strong differentiation-inducing stimulus for the murine myeloid leukaemic cell line, WEHI-3B D+, as well as being a proliferative and differentiative stimulus for normal cells (Nicola, N. A., Metcalf, D., Matsumoto, M. and Johnson, G. R. (1983), *J. Biol. Chem.* 258, 9017–9023). Moreover, Tomida, et. al. (Tomida, M., Yamamoto-Yamaguchi, Y., Hozumi, M., Okabe, T. and Takaka, F. (1986), *FEBS Lett.,* 207, 271–275) have shown that recombinant G-CSF is also able to induce the macrophage differentiation of M1 cells. The relationship between these factors has been a matter of debate. The situation was further complicated by the finding that tumour necrosis factor $\alpha$(TNF$\alpha$) is capable of stimulating the differentiation of the human myeloblastic cell line ML-1 (Takeda, K., Iwamoto, S., Sugimoto, H., Takuma, T., Kawatani, N., Noda, M., Masaki, A., Morise, H., Arimura, H. and Konno, K. (1986) *Nature* 323, 338–340).

In an attempt to resolve the discrepancies between the data of these groups, the present inventors have biochemically fractionated the medium conditioned by Krebs II ascites turnout cells used in a number of previous studies and shown it to contain not only authentic G-CSF and GM-CSF, active on normal Progenitor cells as well as WEHI-3B D+ cells, but also two biochemically distinct, but functionally similar, factors capable of inducing the differentiation of M1 cells. These latter factors have been termed LIF-A and LIF-B because of their ability to suppress the proliferation of M1 leukaemic cells in vitro and it has been shown that they do not induce the differentiation of WEHI-3B D+ cells and do not stimulate the proliferation of normal granulocyte/macrophage progenitor cells.

SUMMARY OF THE INVENTION

LIF, in accordance with the present invention, is defined as a molecule that has the following two properties: (1) it has the ability to suppress the proliferation of myeloid leukaemia cells such as M1 Cells, with associated differentiation of the leukaemic cells; and (2) it will compete with a molecule having the defined sequence of murine LIF or human LIF herein for binding to specific cellular receptors on M1 cells or murine or human macrophages. LIF has the potential for use as a therapeutic non-proliferative agent for suppressing some forms of myeloid leukaemia as well as a reagent for modifying macrophage function and other responses to infections, and clinical testing and research studies relating to these.

The term "polypeptide having LIF activity" as used herein denotes a polypeptide or glycopolypeptide having the properties of LIF as defined above, including but not restricted to polypeptides having an amino acid sequence which is fully or partially homologous with the amino acid sequence of either murine or human LIF as disclosed herein. This term also includes polypeptides which are fully or partially homologous with a portion only of the amino acid sequence of murine or human LIF provided that the polypeptide has the properties of LIF as defined above. This term further includes polypeptides or glycopolypeptides produced by expression in a host cell which are inactive when expressed but which are processed by the host cell to yield active molecules, as well as polypeptides or glycopolypeptides which are inactive when expressed but which are selectively clearable in vitro or in vivo to yield active molecules.

Murine LIF is a molecule having the following biological properties:
(a) induction of macrophage differentiation in cells of the murine myeloid leukaemic cell line M1 with loss of proliferative capacity and death of the clonogenic leukaemic cells, an action potentiated by G-CSF;
(b) selective binding to high affinity receptors on M1 cells and on normal murine monocytes and macrophages from the peritoneal cavity, spleen and bone marrow, with the number of receptors increasing with macrophage maturation or functional activation, but not-to granulocytic, erythroid or lymphoid cell from these tissues;

(c) specific binding of $^{125}$I-LIF to high affinity receptors is not competed for by G-CSF, GM-CSF, Multi-CSF (interleukin-3), M-CSF, interleukins 1,2, 4 or 6, endotoxin or a variety of other growth factors, but is competed for by unlabeled LIF.

(d) elevation by bacterial endotoxin in the serum of normal or athymic mice, but not in endotoxin-resistant C3H/HeJ mice;

(e) production by various tissues including lung, salivary gland, peritoneal cells and bone shaft;

(f) reduction of the survival time in vitro of normal granulocyte-macrophage progenitor cells when grown in the absence of CSF;

(g) an inability to suppress proliferation or induce differentiation of WEHI-3B D+ murine myeloid leukaemic cells, murine myeloid cells transformed to leukaemogenicity by infection with retroviruses expressing GM-CSF or Multi-CSF, the murine leukaemic cell lines WEHI265 and WR19;

(h) no ability to stimulate the proliferation of normal progenitor cells of the granulocyte, macrophage, eosinophil, megakaryocyte, erythroid and mast cell lineages, and an inability to suppress the clonal proliferation or alter the quantitative responsiveness to stimulation by CSFs in vitro of progenitors of normal granulocytes, macrophages, megakaryocytes, eosinophils or natural cytotoxic cells or the proliferation of cells of the continuous cell lines 32CD1.13 and FDCP-1;

(i) an inability to compete with the iodinated derivatives of granulocyte colony-stimulating factor (G-CSF) for binding to specific cellular receptors despite the ability of G-CSF to induce differentiation in M1 and WEHI-3B D+ murine myeloid leukaemic cells and to potentiate the action of LIF on M1 cells;

(j) an inability of the action of LIF to be inhibited by antisera specifically raised against tumour necrosis factor (TNF);

(k) transcripts for murine LIF are present constitutively in the cytoplasm of LB3 and E9.D4 T cells, are not induced by the lectin concanavalin A in these cells, and are present in a number of other cell types;

Murine LIF has also been determined to have the following properties:

(l) a single subunit glycoprotein with molecular weight of $58,000 \pm 5,000$ as determined by electrophoresis in 8–25% gradient polyacrylamide gels containing sodium dodecyl sulphate with or without reducing agent (2-mercaptoethanol or dithiothreitol), and a molecular weight of $23,000 \pm 5,000$ after treatment with the endoglycosidase, N-glycanase;

(m) an isoelectric point between 8.6 and 9.3;

(n) the primary amino acid sequence detailed in FIGS. 10, 11 and 15 herein;

(o) is encoded by the nucleotide sequence detailed in FIGS. 10, 11 and 15 herein;

(p) a specific activity of $1-2 \times 10^8$ units/mg (where 50 units are defined as the amount of LIF which in one milliliter induces a 50% reduction in the clone formation by murine M1 myeloid leukaemic cells);

(q) is encoded by a unique gene on, murine chromosome 11 (as determined by analysis of a panel of mouse/Chinese hamster ovary somatic cell hybrids) bounded by restriction endonuclease cleavage sites as illustrated in FIG. 19 herein;

(r) is homologous to a human gene sequence bounded in chromosomal DNA by restriction endonuclease cleavage sites as illustrated in FIG. 27 herein.

Human LIF is a molecule having the following biological properties of the native and/or yeast derived recombinant product:

(a) induction of macrophage differentiation in cells of the murine myeloid leukaemia cell line M1, with loss of proliferative capacity and death of the clonogenic leukaemia cells;

(b) no ability to stimulate the proliferation of normal human progenitor cells of the granulocyte, macrophage, eosinophil and erythroid lineages;

(c) an ability in combination with G-CSF to partially suppress the proliferation of cells of the human leukaemic cell line U937 and in combination with GM-CSF the proliferation of the human leukaemic cell lines U937 and HL60;

(d) binds specifically to murine LIF receptors on M1 cells and murine macrophages and competes completely for the binding of murine $^{125}$I-LIF to such cells.

(e) binds to specific cellular receptors on the human hepatoma cell line Hep-2G.

Human LIF has also been determined to have the following properties:

(f) is identical to murine LIF at approximately 80% of amino acid residues in the mature protein;

(g) the primary amino acid sequence detailed in FIGS. 25, 26 and 29 herein;

(h) is encoded by a unique gene bounded in chromosomal DNA by restriction endonuclease cleavage sites as illustrated in FIG. 27 herein;

(i) has as a portion of the sequence of its gene, the nucleotide sequence detailed in FIG. 25 herein.

In a first aspect of the present invention, there is provided leukaemia-inhibitory factor (LIF), in essentially pure form. This invention also provides methods for the production of essentially pure LIF, particularly for the production of essentially pure murine LIF by purification from Krebs II ascites tumour cells, and of essentially pure human LIF by purification from the human bladder carcinoma cell line 5637 (ATCC No. HTB 9). Essentially pure LIF may also be produced by host cells, such as yeast cells, mammalian cells and *E. coli*, containing recombinant DNA molecules coding for the amino acid sequence of LIF, or part thereof The references herein to "in essentially pure form" denote a form of polypeptide or glycopolypeptide in which at least 90% of the polypeptide or glycopolypeptide appear as a single band when electrophoresed on an appropriate sodium dodecyl sulphate polyacrylamide gel, said band being coincident with LIF activity.

In another aspect there is provided a method for isolation of recombinant DNA clones containing nucleotide sequences encoding the LIF protein, either completely or in part. The present invention also relates to a nucleotide sequence which has the capacity to encode the unique sequence of amino acids determined to be characteristic of LIF and to furthermore allow the complete amino acid sequence of LIF to be inferred.

In yet another aspect, this invention extends to recombinant DNA molecules containing the aforementioned nucleotide sequences encoding LIF (or substantially similar analogues thereof), either completely or in part, in a form in which said nucleotide sequences are able to direct the synthesis and production of LIF, either completely or in part. This aspect of the invention also extends to cloning vectors (such as plasmids) and host cells having such recombinant DNA molecules inserted therein. Furthermore, the invention also extends to synthetic LIF, either complete or in part, or substantially similar analogues thereof, produced by expression of such recombinant DNA molecules or by peptide synthesis.

BRIEF DESCRIPTION OF THE DRAWINGS

FIG. 6A and FIG. 6B depict binding of radioiodinated-pure LIF by M1 myeloid leukemia cells in the absence or presence of various competing factors.

FIG. 10 provides the nucleotide sequence of cDNA clone pLIF 7.2b, and its predicted amino acid sequence.

FIG. 11 compares the predicted C-terminal sequence encoded by cDNA clone pLIF 7.2b with sequences of known fragments of LIF.

FIG. 12 shows how the murine LIF cDNA was modified for expression in YEpsec1.

FIG. 13A shows concentration dependent induction of M1 colony formation. FIG. 13B shows concentration dependent suppression of colony formation.

FIG. 15A and 15B provide the nucleotide sequence of the LIFcDNA in clone pLIFNK3.

FIGS. 25A, 25B and 25C provide the sequence of the human LIF cDNA clone.

FIG. 26A and 26B compare the amino acid sequences of human and mouse LIF.

FIG. 29A and 29B provide the nucleotide sequence of a synthetic human LIF gene.

FIG. 33A, FIG. 33B and FIG. 33C compare the ability of various DEAE-Sepharose CL-6B fractions of said media to induce differentiation of M1 cells.

FIG. 34A, FIG. 34B and FIG. 34C illustrate the ability of fractions of medium conditioned by the human bladder carcinoma cell line 5637 to induce the formation of differentiated colonies of murine M1 cells.

DETAILED DESCRIPTION OF THE INVENTION

Figure 1:
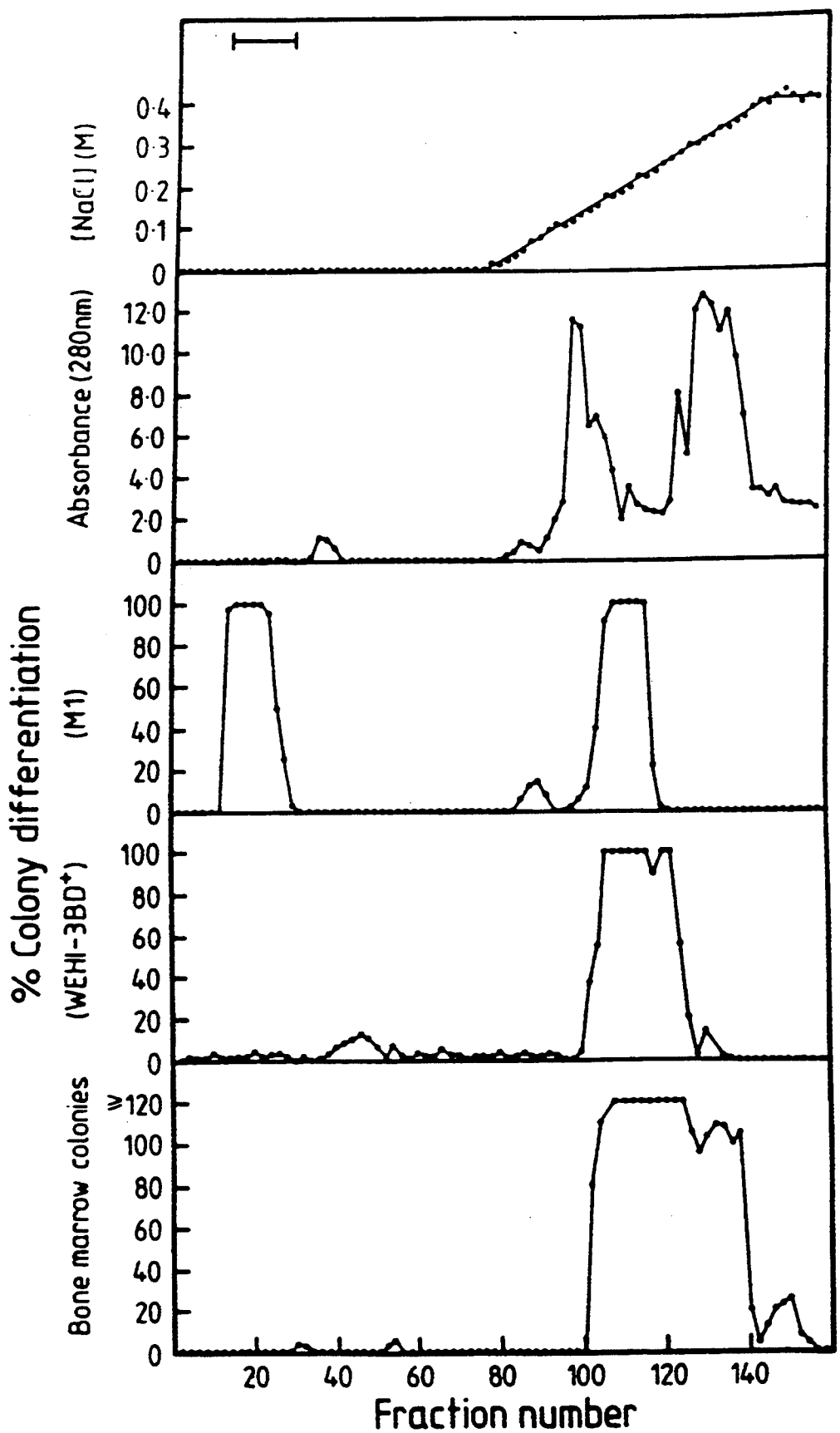
FIG. 1 shows the purification of LIF on DEAE-Sepharose CL-6B (Example 1, step 2).

In the present investigation of LIF, in particular with a view to providing alternative sources of this glycoprotein of both murine and human origin to enable use in clinical and other applications, murine LIF has been purified from Krebs II ascites tumour cells by an efficient purification procedure and has been subjected to partial amino acid sequence analysis as a first step towards chemical or biosynthetic production of this factor.

LIF radioactively derivatized with $I^{125}$ has been used in a receptor competition assay to identify cells and tissues of murine and human origin that synthesize and produce LIF. As a result of this survey, a recombinant DNA library of DNA copies of mRNA from one of these sources has been screened and murine LIF-encoding clones identified by hybridization with radioactively-labelled oligonucleotides encoding portions of the previously determined murine LIF amino acid sequence, and the aforementioned murine LIF cDNA clones subjected to nucleotide sequence analysis. Moreover, the cloned murine LIF encoding sequence has been used as a hybridization probe to identify a human gene encoding a homologue of murine LIF and hybridization conditions established under which said crossspecies hybridization can be effectively performed. As a result, recombinant DNA clones containing DNA sequences encoding the human homologue of murine LIF have been identified.

As a result of this construction of LIF- encoding sequences, recombinant DNA molecules have been constructed that use cloned murine or human LIF-encoding DNA sequences to direct the synthesis of clonally pure LIF, either completely or in part, for example in cultured mammalian cells, in yeast or in bacteria. This invention thus extends to substantially pure LIF produced in this manner.

In one particular embodiment, this invention relates to the-expression of the cloned human and murine LIF genes in yeast cells, in fibroblasts and in E. coli, and to the modification of the cloned gene so that it may be so expressed, as well as to the establishment of the biological and biochemical properties of recombinant human and murine LIF.

In this embodiment also, the present invention relates to recombinant DNA molecules containing nucleotide sequences encoding human or murine LIF (or substantially similar analogues thereof), either completely or in part, in a form in which said nucleotide sequences are able to direct the synthesis and production of human or murine LIF in yeast cells, fibroblasts or E. coli, either completely or in part. This invention also provides cloning vectors (such as plasmids) and host cells having such recombinant DNA molecules inserted therein. Furthermore, the invention extends to synthetic human or murine LIF, either complete or in part, or substantially similar homologues thereof, produced by expression of such recombinant DNA molecules in yeast cells. In one embodiment of the present work relating to LIF, the human and murine LIF gene sequences have been modified and installed in a yeast expression vector, YEpsec1. Yeast cells have been transformed with the resulting recombinants and the medium conditioned by yeast cells so transformed has been shown to contain a factor with biological properties analogous to those of native human and murine LIF.

In view of the potential of LIF for use in the treatment of patients with some forms of myeloid leukaemia and patients with certain infections, the present invention also extends to pharmaceutical compositions comprising LIF, particularly human LIF, either completely or in part, produced for example using cloned LIF-encoding DNA sequences or by chemical synthesis, and to pharmaceutical compositions of analogues of LIF, for example produced by chemical synthesis or derived by mutagenesis of aforesaid cloned LIF-encoding DNA sequences. The pharmaceutical compositions may also contain at least one other biological regulator of blood cells, such as G-CSF or GM-CSF. Furthermore, the invention also extends to diagnostic reagents for use in detecting genetic rearrangements, alterations or lesions associated with the human LIF gene in diseases of blood cell formation, including leukaemia and congenital diseases associated with susceptibility to infection.

EXAMPLE 1

The accompanying FIGS. 1 to 5 relate to various steps of the purification method described below, showing where LIF is pooled in each fractionation step and showing evidence of its purity. In the Figures:

FIG. 1: relates to Step 2 of the purification of LIF on DEAE-Sepharose CL-6B. The bar indicates fractions that are pooled for Step 3.

Figure 2:
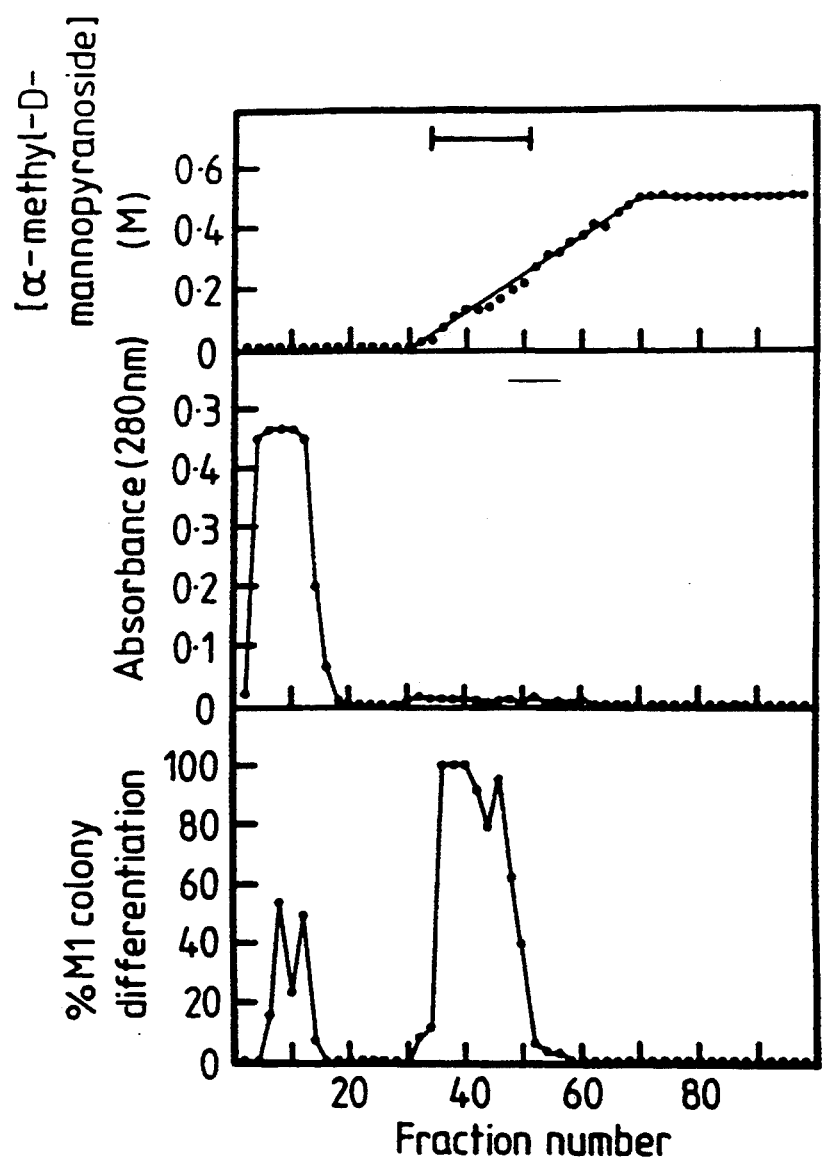
FIG. 2 shows the further purification of LIF on lentil lectin Sepharose 4B (Example 1, step 3).

FIG. 2: relates to Step 3 of the purification of LIF on Lentil lectin Sepharose 4B. The bar indicates fractions that are pooled.for Step 4.

Figure 3:
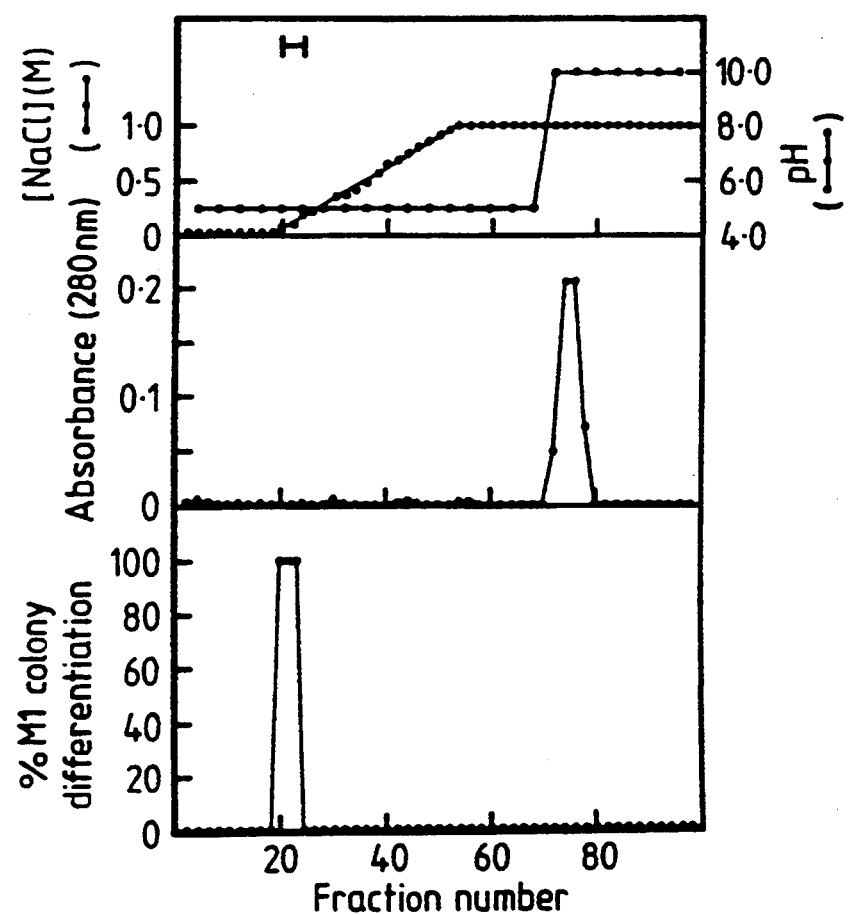
FIG. 3 shows the further purification of LIF on CM-Sepharose C1-6B (Example 1, step 4).

FIG. 3: relates to Step 4 of the purification of LIF on CM-Sepharose CL-6B. The bar indicates fractions that are pooled for Step 5.

Figure 4:
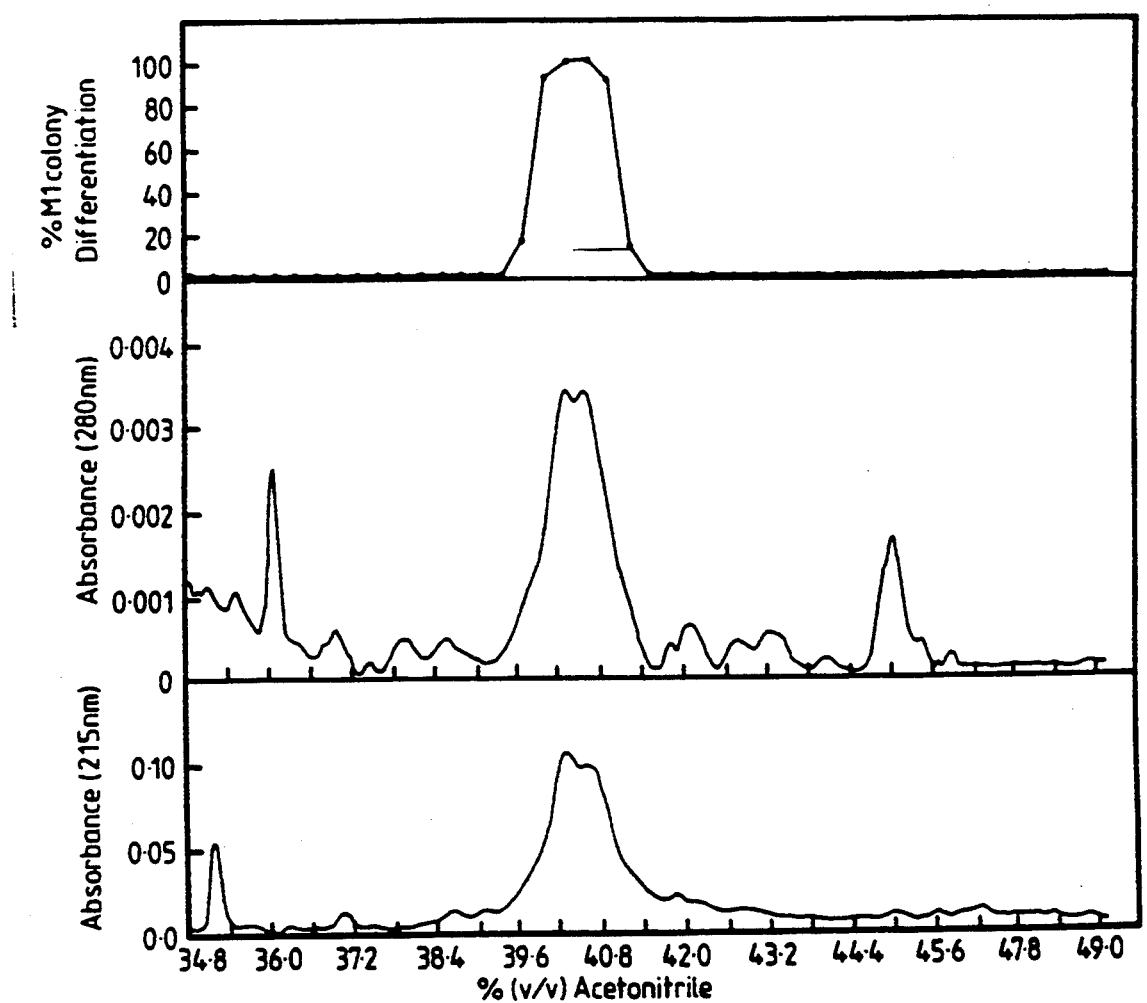
FIG. 4 shows the further purification of LIF by HPLC (Example 1, step 5).

FIG. 4: relates to Step 5 of the purification of LIF on a fatty acid analysis HPLC column. Fractions from 39.6 to 41.3% acetonitrile are pooled.

Figure 5:
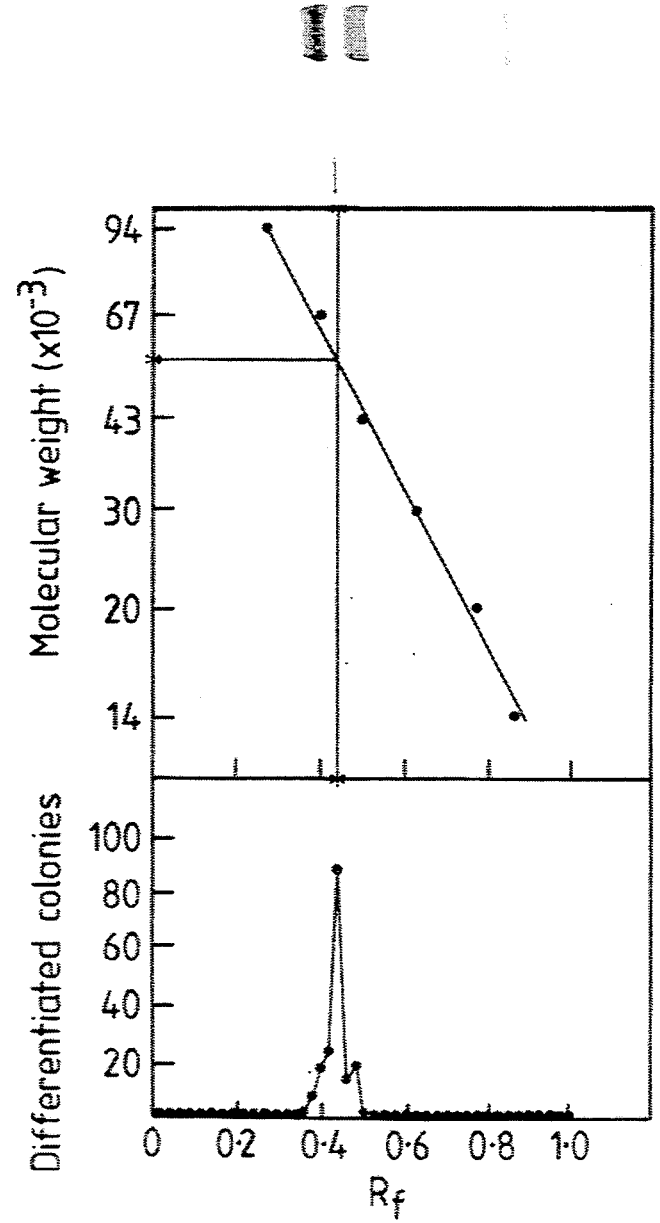
FIG. 5 compares the molecular weight of protein standards and purified LIF as determined by SDS-PAGE. The upper panel graphically illustrates-the migration of protein standards (93,000; 67,000; 43,000; 30,000; 20,000; and 14,000 molecular weight) and purified LIF (two preparations) on 8–25% polyacrylamide gel. The corresponding gel profiles are depicted above the upper panel, and positioned such that protein bands are aligned with the corresponding molecular weight positions on the graph, i.e., the bottom of the gel is at the right. The top lane of the gel shows the migration of protein standards, and the middle and bottom lanes of the gel show the migration of purified LIF. The lower panel of FIG. 5 depicts the biological activity, as measured by differentiated colonies, of protein extracted from gel strips of a parallel lane of the gel loaded with LIF.

FIG. 5: shows the molecular weight and purity of purified LIF. The upper panel shows the migration of protein standards (93,000; 67,000; 43,000; 30,000; 20,000 and 14,000 molecular weight) and purified LIF (two preparations) on 8–25% polyacrylamide SDS gel. The protein and biological activity are both associated with a protein of molecular weight 58,000.

Step 1

Krebs II turnout cells ($1 \times 6^6$) are injected intraperitoneally into C57B16/6fj/ WEHI mice and after 7 days the mice are sacrificed and the peritoneal fluid removed. The cells are centrifuged, resuspended at $5 \times 10^6$ cells/ml in Dulbecco's modified Eagle's medium containing E. coli lipopolysaccharide (200 ng/ml) and incubated for 24 hrs at 37° C. in a humidified incubator containing 10% $CO_2$ in air. The cells are again centrifuged, the conditioned medium removed, made up to 0.02% (w/v) sodium azide and stored at 4° C., Thirty-six liters of conditioned medium are concentrated to 100 ml using a HIP10-8 hollow fibre cartridge in an Amicon DC2A concentrator, exchanged into 10 mM Tris-HCl buffer pH8.0 containing 1 mM phenylmethyl sulphonyl fluoride (PMSF), sodium azide (0.02% w/v) and Tween 20 (0.02% v/v) and re-concentrated to 20 ml over a YM-10 membrane in an Amicon stirred cell.

Step 2

The concentrate is applied to a column (2.5×30 cm) of DEAE-Sepharose CL-6B (Pharmacia) equilibrated in the same buffer and eluted with 200 ml of equilibration buffer followed by a 400 ml linear gradient to 0.3M NaCl in the same buffer. The flow rate is 25 ml/hr and 5.8 ml fractions are collected and assayed. (See FIG. 1)

Step 3

The fractions of protein which failed to bind to the gel during the pre-gradient step and which contained activity on murine M1 cells are pooled, concentrated over a YM-10 membrane, exchanged into 100 mm sodium acetate buffer pH6.0 containing 1 mM $MgCl_2$, 1 mM PMSF, 0.2% sodium azide and 0.02% Tween 20 and applied to a column (1×4 cm) of Lentil lectin-sepharose 4B (Pharmacia) equilibrated in the same buffer. The column is eluted with 25 ml of equilibration buffer and then a 100 ml linear gradient to 0.5M =-methyl-D-mannopyranoside in the same buffer at a flow rate of 10 ml/hr. Fractions of 3 ml are collected and assayed. (See FIG. 2)

Step 4

The fractions of proteins which bind to the gel and are eluted by the sugar and have activity on M1 cells are pooled, concentrated and exchanged into 100 mM sodium acetate buffer pH5.0- containing 1 mM PMSF, 0.02% sodium azide and 0.02% Tween 20 and applied to a column (1.0×4.0 cm) of CM-Sepharose CL-6B (Pharmacia) equilibrated in the same buffer. The column is eluted with 25 ml equilibration buffer and then a 100 ml linear gradient to 1.0m NaCl in the same buffer and then by 25 ml of 1.0M NaCl adjusted to pH10 with NaOH. The flow rate is 2.0 ml/hr and 3.0 ml fractions are collected. (see FIG. 3)

Step 5

The fractions of proteins which bind to the gel and are eluted by the NaCl gradient and have activity on M1 cells are pooled, concentrated to 2 ml over a YM-10 membrane and exchanged into 20 mM ammonium acetate buffer pH5.0 containing 0.02% Tween 20 and then filtered through a 0.45μ Millipore filter. The pool is loaded into the injector of a high performance liquid chromatography system (Beckman) equipped with a Waters fatty acid analysis column and dual pumps with gradient programmer. The column is equilibrated in water containing 0.1% (v/v) trifluoroacetic acid (TFA), the sample is injected, and the column is then eluted with a 5 min linear gradient to 34.8% (v/v) acetonitrile in water and 0.1% TFA and then eluted with a 50 min linear gradient to 49.8% (v/v) acetonitrile in water and 0.1% TFA. The flow rate is 1 ml/min and 1 ml fractions are collected into polypropylene tubes containing 50 μl of 100 mM ammonium bicarbonate and 0.4 % Tween 20. (see FIG. 4).

The fractions with activity on M1 cells from step 5 consisted of two overlapping ultraviolent- absorbing peaks. Each peak was associated with activity on M1 cells and each peak corresponded to a single protein band of Mr 58,000 on sodium dodecyl sulphate polyacrylamide gels using silver staining. In each case, the protein band of Mr 58,000 contained the biological activity on M1 cells as assessed by cutting a parallel track on the gel (also loaded with LIF) into 1 mm strips, extracting the protein from the gel strips and assaying the extracted protein for its ability to suppress proliferation and induce differentiation in M1 cells in semi-solid agar cultures. (see FIG. 5).

EXAMPLE 2

The following Example sets out the steps used in obtaining the N-terminal amino acid sequence and amino acid sequences of various peptides generated by proteolytic cleavage with trypsin or Staphylococcal V8 protease.

LIF purified by the procedure of Example 1 (15 μg) was applied to a microbore (2 mm) column packed with Brownlee RP300 beads (C8) and eluted on a HPLC system with a linear gradient from 0–60% acetonitrile in 0.1% trifluoroacetic acid. The protein eluted as a single peak in a volumn of 100 μl. This was applied to a glass fibre disc and allowed to dry and then placed in the sequencing chamber of an Applied Biosystem (Model 470A) gas phase protein sequencer. The protein was sequenced by Edman chemistry and the phenylthiohydantoin derivatives of the individual amino acids identified by HPLC on an Applied Biosystems 120A PTH analyser.

A separate aliquot of LIF (20 μg) also purified by the aforementioned procedure, was diluted to 2 ml in 6m guanidine hydrochloride, 0.2M Tris-HCL buffer pH8.5, 2 mM dithiothreitol and incubated at 37° C. for 2 hrs. Then a 30-fold molar excess of iodoacetic acid was added and the solution incubated at 37° C. for a further 15 min. The solution was applied to the same microbore HPLC column and eluted as described above. The reduced and carboxy-methylated derivative of LIF (RCM-LIF) eluted 3 min later from the column than the untreated LIF and RCM-LIF (200 μl) was diluted to 1 ml with 0.1M Tris-HCL buffer pH8.0 containing 0.02% Tween 20, 1 mM $CaCl_2$ and 2 μg of TPCK-treated trypsin. This incubation was allowed to proceed for 18 hr at 37° C. and the mixture was again applied to the microbore column and eluted in the same way as described above. Individual peptides appeared as UV-absorbing peaks, and were collected individually. Some of these peptides were sequenced directly as described above while others were repurified on the same column but using an 0–60% acetonitrile gradient in 0.9% NaCl pH6.0 before being sequenced.

A second aliquot of RCM-LIF (200 μl=10 μg) was diluted to 1 ml with 0.05M sodium phosphate buffer, pH 7.8 containing 0.002M EDTA and 0.02% Tween 20, and was digested with 2 μg of Staphylococcus aureus V8 protease for 18 hours at 37° C. The reaction mixture was applied to the same microbore column and eluted as described above.

The 26 amino acids defining LIF from the amino terminal in sequence were found to be:
N-Pro-Leu-Pro-Ile-Thr-Pro-Val-X-Ala-Thr-X-Ala-Ile-Arg-His-Pro-Cys-His-Gly-Asn-Leu-Met-Asn-Gln-Ile-Lys The amino acid sequences of several tryptic peptides were found to be:
1. His-Pro-Cys-His-Gly-Asn-Leu-Met-Asn-Gln-Ile-Lys
2. Met-Val-Ala-Tyr . . .
3. Gly-Leu-Leu-Ser-Asn-Val-Leu-Cys . . .
4. Leu-Gly-Cys-Gln-Leu-Leu-Gly-Thr-Tyr-Lys
5. Val-Leu-Asn-Pro-Thr-Ala-Val-Ser-Leu-Gln-Val-Lys
6. Asn-Gln-Leu-Ala-Gln-Leu-X-Gly-Ser-Ala-Asn-Ala-Leu-Phe-Leu-Val-Glu-Leu-Tyr . . .
7. Leu-Val-Ile-Ser-Tyr . . .
8. Val-Gly-His-Val-Asp-Val-Pro-Val-Pro-Asp-His-Ser-Asp-Lys-Glu-Ala-Phe-Gln.
9. Leu-X-Ala-Thr-Ile-Asp-Val-Met-Arg.
10. Gln-Val-Ile-Ser-Val-Val-X-Gln-Ala-Phe.

The amino acid sequence of a peptide generated by digestion of LIF with the V8 protease was:
Ala-Phe-Gln-Arg-Lys-Lys-Leu-Gly-Cys-Gln-Leu-Leu-Gly-Thr-Tyr-Lys-Gln-Val-Ile-Ser-Val-Val-Val-Gln-Ala-Phe.

EXAMPLE 3

The following Example sets out the steps used to obtain radioactively-derivatized LIF and to identify sources of LIF by a receptor competition assay.

The accompanying FIG. 6 relates to Example 3: Binding of radioiodinated-pure LIF (approximately $2 \times 10^5$ cpm/ng) to M1 myeloid leukaemia cells at 0° C. M1 cells ($5 \times 10^6$) were incubated with $^{125}I$-LIF ($4 \times 10^5$ cpm) with or without competing factors for 2 hours after which bound radioactivity was separated from unbound radioactivity by centrifugation through foetal calf serum. A. Titration of unlabelled pure LIF and pure Multi-CSF, GM-CSF, G-CSF or M-CSF as competing factors at the indicated dilutions (10 μl of each dilution added to a final volume of 80 μl).

The highest concentrations of each were $10^4$ units/ml; $3.5 \times 10^4$ units/ml; $3 \times 10^4$ units/ml; $5 \times 10^4$ units/ml; $4 \times 10^4$ units/ml; respectively. B. Ability of pure LIF or lipopolysaccharide (LPS) or concentrated (4-8-fold) media conditioned by various cells or serum from endotoxin-injected mice to compete for the binding of $^{125}I$-LIF to M1 cells as above.

LIF, purified from Krebs II ascites cell conditioned medium as described in Example 1, was radioactively labelled with $^{125}$I on tyrosine residues as described previously (Nicola, N. A. and Metcalf, D., *J. Cell. Physiol.* 128:180–188, 1986) producing $^{125}$I-LIF with a specific radioactivity of approximately $2 \times 10^5$ cpm/ng. $^{125}$I-LIF bound specifically to M1 myeloid leukaemic cells as well as murine adult bone marrow, spleen, thymus and peritoneal exudate cells. Cell autoradiographic analysis indicated that $^{125}$I-LIF bound specifically only to macrophages and their precursor cells, with receptor numbers increasing with cell maturation, and not detectably to any other haemopoietic cell type. This suggests that LIF might have clinically useful applications in modulating macrophage function in a variety of disease states. The specific binding of $^{125}$I-LIF to M1 myeloid leukaemic cells or to peritoneal macrophage populations was inhibited by unlabelled LIF, but not by a range of other haemopoietic growth factors, including G-CSF, GM-CSF, M-CSF (CSF-1), Multi-CSF (interleukin 3), interleukins 1,2,4,6, endotoxin or other growth factors (see for example FIG. 6). The ability of cell conditioned media or cell extracts to inhibit the binding of $^{125}$I-LIF to such cell populations (radioreceptor assay for LIF) (FIG. 6B) thus provides a specific assay for the presence of LIF production or storage by various cells and tissues. For example, medium conditioned by lectin-activated LB3 T cells strongly inhibited specific binding of $^{125}$I-LIF to M1 cells thus indicating that LB3 cells produce LIF.

EXAMPLE 4

The following Example sets out the steps used to obtain a cloned complementary DNA copy of the mRNA encoding murine LIF.

Figures 7, 8:
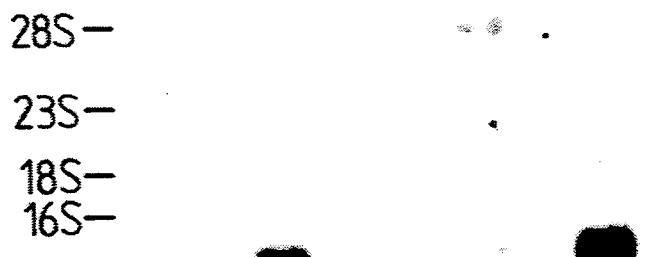
FIGS. 7(A and B) depict mRNA in conA-stimulated cells using radioiodinated GM-CSF or Multi-CSF probes.
FIG. 8 schematizes the design of the anti-LIF gene probe.

The accompanying FIGS. 7 to 10 relate to various steps of the method described below. In the Figures:

FIG. 7 relates to Step 1 of the cloning of LIF cDNA clones: the accumulation of mRNAs for haemopoietic growth regulators in the cytoplasm of LB3 cells following stimulation with the lectin concanavalin A. Cytoplasmic polyadenylated RNA (5 μg) from WEHI-3B D− cells (track 1), T cell clone LB3 cells cultured at $10^6$ cells/ml with 5 μg/ml concanavalin A for 5 hours (track 2), and unstimulated LB3 cells (track 3) was electrophoresed on formaldehyde agarose gels, transferred to nitrocellulose and hybridized with a $^{32}$P-GM-CSF probe (panel a) or a $^{32}$P-Multi-CSF probe (panel b) (for details see Kelso, A., Metcalf, D. and Gough, N. M. *J. Immunol.* 136:1718–1725, 1986).

FIG. 8 relates to Step 3 of the cloning of LIF cDNA clones: Synthetic oligonucleotide used for identifying LIF clones. A portion of the amino acid sequence of murine LIF near the N-terminus (residues 15–26, see Example 2) is shown on the top line, the possible combinations of mRNA sequences that could encode this peptide in the middle, and the oligonucleotide probe complementary to this mRNA sequence, below. Note that for all amino acid residues except Cys 17 and His 18, the oligonucleotide is complementary only to the codons most frequently used in mammalian coding regions (Grantham et. al., *Nucleic Acids Res.* 9:43–77, 1981). For Cys 17, the sequence is complementary to both codons. For His 18, the oligonucleotide is complementary to the less frequent CAU codon. It was considered unlikely that the CAC codon would be used as it would generate, in conjunction with the neighbouring Ely codon, the infrequent CpG dinucleotide (Swartz et. al, *J. Biol. Chem.* 238:1961–1967, 1962)

Figure 9:
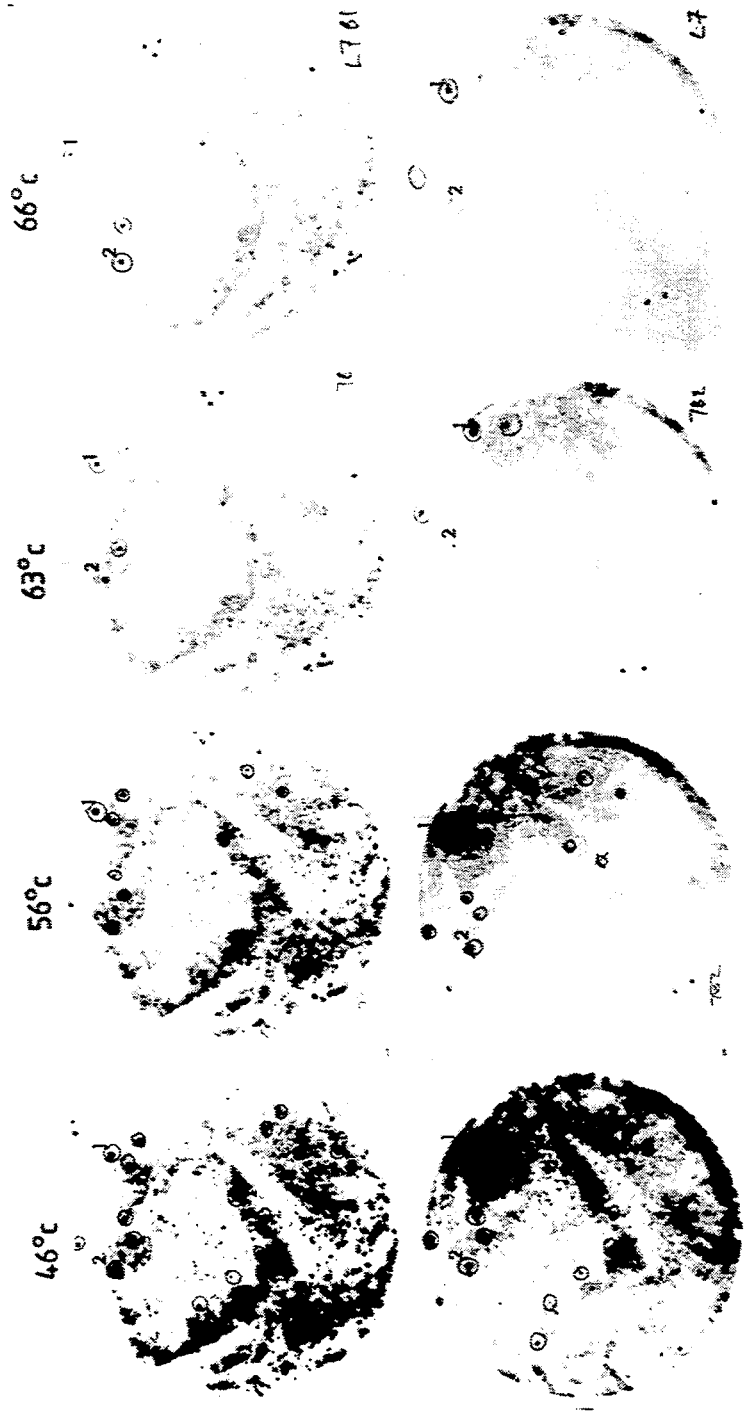
FIG. 9 shows hybridization of the anti-LIF probe to cDNA clones at different temperatures.

FIG. 9 relates to Step 4 of the cloning of LIF cDNA clones; the identification of LIF cDNA clones by hybridization with the oligonucleotide illustrated in FIG. 8.

FIG. 10 relates to Step 5 of the cloning of LIF cDNA clones: nucleotide sequence of cDNA clone pLIF7.2b and LIF amino acid sequence. The sequence of the mRNA-synonymous strand of the cDNA is listed 5′ to 3′ with the predicted amino acid sequence of LIF given above; numbers at the end of lines indicate the position of the final residue (amino acid or nucleotide) on that line. The amino acid sequence is numbered consecutively from the first residue encoded in this clone. Regions of amino acid sequence determined by analysis of the protein are overlined; there are no discordancies between the two. Pro 9 was the N-terminal residue determined by direct amino acid sequence analysis (Example 2.). Seven potential N-linked glycosylation sites (Neuberger, A. et al in *Glycoproteins,* Gottschalk, A, ed., Elsevier, Amsterdam, pp 450–490, 1972) are indicated with asterisks and four potential O-linked glycosylation sites (Takahashi, N. et al, *Proc. Natl. Acad. Sci. USA,* 81: 2021–2025, 1984) with hatches.

Step 1

Preparation of RNA Containing the LIF mRNA

Cells of the cloned murine T cell line LB3 (Kelso, A. and Metcalf, D. *Exptl. Hematol.* 13:7–15, 1985) were stimulated with the lectin concanavalin A for 6 hours to enhance the accumulation in the cytoplasm of mRNAs encoding various factors which regulate the growth and differentiation of haemopoietic cells. (Kelso, A., Metcalf, D. and Gough, N. M. *J. Immunol.* 36:1718–1725, 1986). (For example, FIG. 7 shows the increased production of mRNAs encoding the haemopoietic growth factors GM-CSF and Multi-CSF in cells so stimulated). Cytoplasmic RNA was prepared from $5 \times 10^8$ concanavalin A-stimulated LB3 cells using a technique described previously (Gough, N. M. *J. Mol. Biol.* 165:683–699, 1983). Polyadenylated mRNA molecules were partitioned from ribosomal RNA by two cycles of chromatography on oligo-dT cellulose using standard procedures (Maniatis, T. et.al., *Molecular Cloning,* Cold Spring Harbor, New York, 1982).

It was found subsequently by Northern blot analysis that unlike the mRNAs for GM-CSF and Multi-CSF, the LIF mRNA is present constitutively in LB3 cells and its abundance is not enhanced by concanavalin A stimulation (Gearing D. P. et al. *EMBO J.* 6: 3995–4002, 1987).

Step 2

Synthesis and Cloning of a Library of LB3 cDNA Molecules

Double-stranded DNA copies of the LB3 mRNA prepared as described above were synthesized by standard procedures (Maniatis, T. et. al., *Molecular Cloning,* Cold Spring Harbor, New York, 1982 and Gough, N. M. et. al. *Nature* 309:763–767, 1984). Briefly, 10 μg of cytoplasmic polyadenylated LB3 mRNA were used as a template for synthesis of single-stranded complementary DNA (cDNA) in a reaction catalyzed by arian myeloblastosis virus reverse transcriptase and primed with oligo-dT. After completion of this reaction, the mRNA was degraded by incubation at 65° C. for 1 hour in 0.3M NaOH, 1 mM EDTA. After neutralisation of the base and recovery of the cDNA by ethanol precipitation, the single-stranded cDNA was converted to duplex form in a reaction catalyzed by the Klenow fragment of *E. coli* DNA polymerase I. The "hairpin loop" structure of the cDNA was then cleaved by treatment with the single-strand specific nuclease S1 and then tails of deoxycytidine residues (approximately 20–30 residues long) were appended to each end of the double-stranded cDNA using the enzyme terminal deoxynucleotidyltransferase as described (Michelson, A. M. and Orkin, S. *J. Biol. Chem.* 257:14773–14782, 1982). The dC-tailed cDNA was fractionated by electrophoresis on a 1.5% agarose gel and molecules greater than 500 bp in length recovered and annealed to a plasmid DNA molecule (pJL3, Gough, N. M. et. al., *EMBO J.* 4: 645: 653, 1984) that had been cleaved with the restriction endonuclease Sac 1 and to which tails of deoxyguanosine residues had been appended (Michelson, A. M. and Orkin, J., *J. Biol. Chem.* 257:14773–14782, 1982). The tailed cDNA and plasmid molecules were annealed as described (Gough, N. M. et.al., *Biochemistry* 19:2702–2710, 1980) and *E. coli* MC1061 (Casadaban, M. and Cohen, S., *J. Mol. Biol.* 138: 179–207, 1980) transformed with the annealed cDNA/plasmid mixture and approximately 50,000 independently transformed bacterial colonies selected by growth on agar plates containing 10 μg/ml ampicillin. The transformed bacterial colonies were removed from the agar plates by washing with liquid growth medium containing 50 μg/ml ampicillin and stored as 10 independent pools in 10% glycerol at −70°.

Step 3

Design of Oligonucleotide Probes

A sequence of 26 amino acids at the amino terminus of LIF and residues from 11 different peptides derived by digestion of LIF with trypsin and V8 protease have been determined (see Example 2). These amino acid sequences provided the basis for the design of oligonucleotides complementary to certain defined regions of the mRNA encoding LIF for use as hybridization probes to identify cDNA clones corresponding to the LIF mRNA.

Each naturally occurring amino acid is encoded in its corresponding mRNA by a specific combination of 3 ribonucleoside triphosphates (a codon) (eg Watson, J. *Molecular Biology of the Gene*, 3rd ed., Benjamin/Cummings, Menlo Park, Calif., 1976). Certain amino acids are specified by only one codon, whereas others are specified by as many as 6 different codons (eg Watson, J. *Molecular biology of the Gene*, supra). Since therefore a large number of different combinations of nucleotide sequences could in fact encode any particular amino acid sequence, a large number of different degenerate oligonucleotides would need to be constructed in order to cater for every possible sequence potentially encoding that peptide. There are however, certain technical constraints in the use of highly degenerate oligonucleotides as hybridization probes. However, since for a given amino acid not all codons are employed with equivalent frequency (Grantham, R. et. al. *Nucleic Acids Res.* 9:43–73, 1981) and since in the mammalian genome the CpG dinucleotide is underrepresented, occurring at only 20–25% of the frequency expected from base composition (Swartz, M. N. et. al., *J. Biol. Chem.* 238:1961–1967, 1962), it is often possible to predict the likely nucleotide sequence encoding a given peptide and thus reduce the complexity of a given oligonucleotide probe. Given the foregoing considerations, a number of oligonucleotides corresponding to different LIF peptides were designed and synthesized by standard procedures.

Step 4

Screening of an LB3 cDNA Library for LIF-Encoding Clones

For screening colonies of bacteria by hybridization with oligonucleotide probes, 10,000–15,000 bacterial colonies from each pool of the aforementioned LB3 cDNA library were grown on agar plates (containing 50 μg/ml ampicilin), transferred to nitrocellulose filter disks and plasmid DNA amplified by incubation of the filters on agar plates containing 200 μg/ml chloramphenicol (Hanahan, D. and Meselson, M. *Gene* 10:63–67, 1980). After regrowth of colonies on the original plate, a second nitrocellulose filter was prepared as above. The master plate was regrown a second time and then stored at 4° C. Plasmid DNA was released from the bacterial colonies and fixed to the nitrocellulose filters as previously described (Maniatis, T. et. al. *Molecular Cloning*, Cold Spring Harbor, New York, 1982). Before hybridization, filters were incubated for several hours at 37° C. in 0.9M NaCl, 0.09M sodium citrate, 0.2% Ficoll., 0.2% polyvinyl-pyrollidone, 0.2% bovine serum albumin, 50 μg/ml heat denatured salmon sperm DNA, 50 μg/ml *E. coli* tRNA, 0.1M ATP and 2 mM sodium pyrophosphate. Hybridization was performed in the same solution, containing in addition 0.1% NP40, at 37° C. for 18 hours. 500 ng of the synthetic oligonucleotide shown in FIG. 8, was radioactively labelled in a reaction catalyzed by polynucleotide kinase and containing 500 μCi of [γ-$^{32}$P]ATP (specific activity 2,000–3,000 Ci/mmol). Unincorporated [γ-$^{32}$P]ATP was then separated from the radioactively labelled oligonucleotide by ion exchange chromatography on a NACS-PREPAC column (Bethesda Research Laboratories) according to the manufacturer's instructions. The radioactively labelled oligonucleotide was included in the hybridization reaction at a concentration of approx. 20 ng/ml. After hybridization, filters were washed extensively in 0.9M NaCl, 0.09M sodium citrate, 0.1% sodium dodecyl sulphate at various temperatures (as described below) and after each wash, autoradiographed.

The rationale behind performing successive rounds of washing was that at lower temperatures, all clones having even a small degree of homology with the oligonucleotide (as little as approximately 15 nucleotides) would be revealed as autoradiographic spots appearing on duplicate filters. As the temperature is increased, the oligonucleotide probe would be melted from clones with the lowest level of homology and the corresponding autoradiographic signals would thus be lost. Clones with the highest degree of homology (and thus clones which represent the best candidates for containing LIF cDNA sequences) will retain hybridization at the highest temperature. By this strategy it is thus possible to focus directly on the strongest candidate clones. FIG. 9 shows the performance of a set of clones on a duplicate pair of filters containing 15,000 LB3 cDNA clones as the washing temperature was raised from 46° C. to 66° C. Several clones retained hybridization to the oligonucleotide only at lower temperatures whereas several retained hybridization even at 66° C. (for example, clones 1 and 2). The latter clones were thus selected for further analysis and the corresponding bacterial colonies removed from the master plates, purified and plasmid DNA prepared from each bacterial clone by standard procedures (Maniatis, T. et. al. *Molecular Cloning,* Cold Spring Harbor, 1982). Preliminary structural analysis of these clones (by assessing the size of the inserted cDNA, by mapping the locations of cleavage sites for various restriction endonucleases and by testing for hybridization with various oligonucleotides corresponding to different LIF peptides) indicated that each of these clones were in fact identical; that is, they represented different isolates of the same original cloning event. Thus further detailed analysis was performed on only one clone, pLIF7.2b.

Step 5

Determination of the Nucleotide Sequence of pLIF7.2b

Nucleotide sequence analysis of the cDNA portion of clone pLIF7.2b was performed by the dideoxy chain termination method (Sanger, F. et. al., *Proc. Natl. Acad. Sci. USA* 74:5463–5467, 1977), using alkaline or heat denatured double-stranded plasmid DNA as template, a variety of oligonucleotides complementary both to the regions of the vector (pJL3) flanking the cDNA and to sequences within the cDNA insert as primers, and using both the Klenow fragment of *E. coli* DNA polymerase I and the avian myeloblastosis virus reverse transcriptase as polymerases in the sequencing reactions. The sequence so determined for the cDNA portion of clone pLIF7.2b is shown in FIG. 10. Such analysis confirmed that this clone does indeed contain a DNA copy of a mRNA with the capacity to encode the LIF molecule, since within the only translational reading frame that spans the entire cDNA uninterrupted by stop codons, all of the amino acid sequences previously determined for various peptides of the LIF molecule may be found. This clone does not however contain a complete copy of the LIF coding region since (a) it does not extend at the 5' end through a region encoding a presumed hydrophobic leader sequence initiated by a methionine codon and (b) it does not include at its 3' end an in-frame translational stop codon. It does however extend at the 5' end past the start of the region encoding the mature protein, determined by comparison with the previously determined amino-terminal amino acid sequence (residue Pro 9 in FIG. 10).

EXAMPLE 5

The following sets out the steps used to construct a full length copy of the murine LIF coding region, to install this coding region in a yeast expression vector and to produce murine LIF.

The accompanying Figures relate to various steps of the method described below. In the Figures:

FIG. 11: relates to Step 1 of the expression of murine LIF in yeast cells: C-terminal amino acid sequence of LIF. The amino acid sequence at the C-terminus of the pLIF7.2b reading frame is shown above the sequence of a Staphylococcal V8 protease and a tryptic peptide derived from LIF purified from Krebs ascites tumour cells. Note that these latter peptides extend the pLIF7.2b LIF sequence by 9 amino acids and terminate at the same residue. The nucleotide and amino acid sequence at the corresponding region of clone pLIFNK1 is shown at the bottom line, confirming the C-terminus assigned by direct amino acid sequencing. The numbering system is that of FIG. 10.

FIG. 12: relates to step 2 of the expression of murine LIF in yeast cells: reconstruction of the pLIF7.2b cDNA for insertion into the yeast expression vector, YEpsec1. Partial nucleotide sequence of the pLIF7.2b cDNA and its encoded amino acid sequence are shown on the top line. Numbering is according to FIGS. 10 and 11. The second and third lines show the sequence of pLIFmut1 and pLIFmut2 respectively. Asterisks indicate stop codons. Restriction sites (Bam HI, Hind III and Eco R1) used for cloning into YEpsec1 (Baldari. C. et al, *EMBO J.* 6: 229–234, 1987) and pGEX-2T (Smith, D. B. and Johnson, K. G., *Gene*, in press, 1988) are indicated. The bottom line shows partial sequence of the *K. lactis* killer toxin signal sequence in YEpsec1. The sequence Gly-Ser encoded at the Bam HI restriction site is efficiently recognized by signal peptidase (Baldari, C. et al, *EMBO J.* 6: 229–234, 1987).

FIG. 13: relates to step 4 of the expression of murine LIF in yeast cells: the biological activity of yeast-derived recombinant LIF in cultures of M1 leukaemic cells. Titration in M1 cultures of yeast-derived recombinant LIF (— —) versus purified native LIF-A (—o—) showing similar concentration dependent induction of differentiation in M1 colonies (panel A) and suppression of colony formation (panel B). Each point represents the mean value from duplicate cultures.

Figure 14:
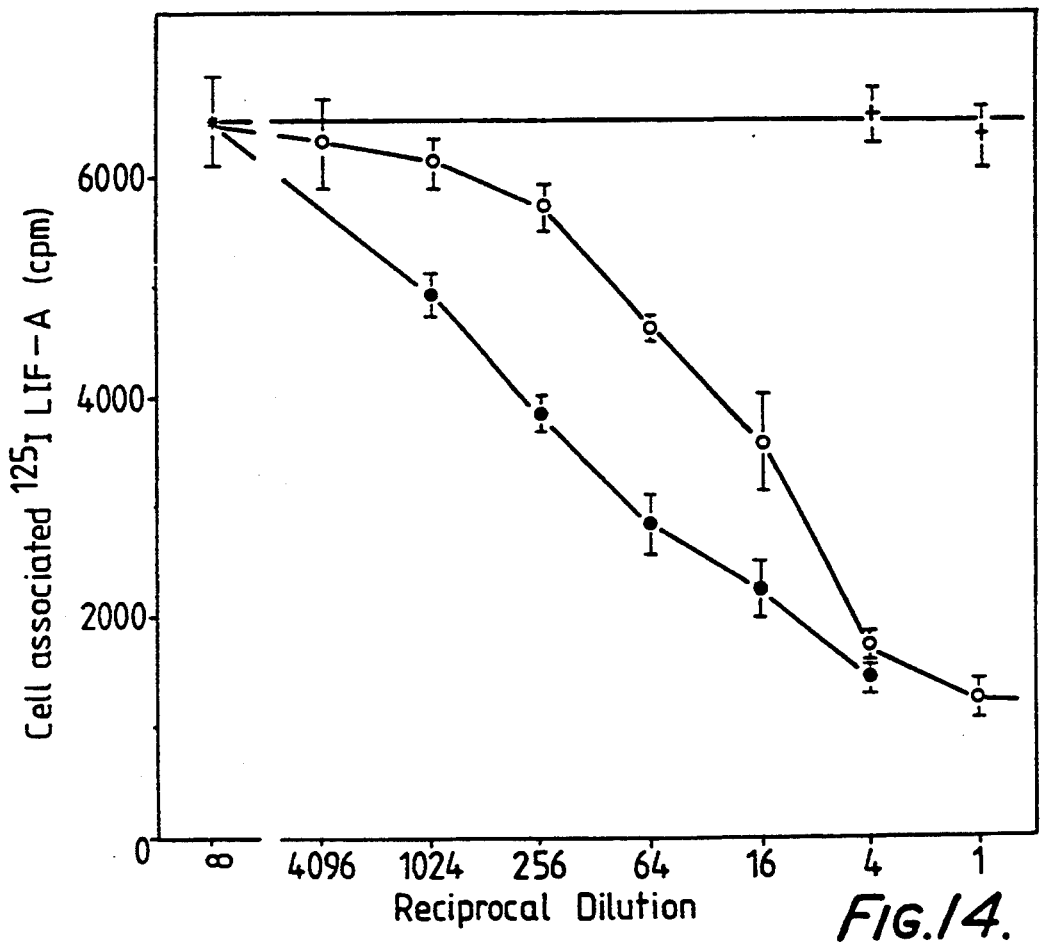
FIG. 14 compares the ability of various LIF preparations to compete with radioiodinated native LIF for cellular receptors on murine peritoneal cells.

FIG. 14: relates to step 5 of the expression of murine LIF in yeast cells: the ability of different dilutions of authentic native murine LIF-A (—o—), conditioned medium from yeast cells containing the LIFmut1/YEpsec1 recombinant induced with galactose (— —) and conditioned medium from the same yeast cells, but not induced with galactose (—+—) to compete for the binding of native $^{125}$I-LIF-A to cellular receptors on murine peritoneal cells.

Step 1

Determination of the Amino Acid Sequence at the C-Terminus of Murine LIF

The cDNA clone pLIF7.2b of Example 4 contains an incomplete copy of the murine LIF mRNA. At the 5' end, the cDNA encodes 8 residues N-terminal to the first residue determined by N-terminal amino acid sequence analysis (Pro 9 in FIG. 10). At the 3' end however, pLIF7.2b is incomplete as it does not contain an in-frame translational stop codon. Inspection of the amino acid sequence of two LIF peptides determined by direct amino acid sequencing (Example 2) suggested that pLIF7.2b was lacking only 27 nucleotides of coding region at the 3' end. As illustrated in FIG. 11, a V8-derived peptide started at residue Ala 162 of the cDNA sequence and extended the amino acid sequence deduced from the cDNA clone by 9 residues. A tryptic peptide contained within the V8 peptide terminated at the same residue, suggesting that Phe 187 is the C-terminal residue of the protein. In order to confirm this conclusion, a LIF cDNA clone overlapping with pLIF7.2b and extending 3'-ward was isolated and subjected to nucleotide sequence analysis.

In order to construct and screen an appropriate cDNA library from which to isolate such a clone, a series of different mRNA samples were screened by Northern blot hybridization to identify the RNA samples with the highest concentration of LIF mRNA molecules. Cytoplasmic polyadenylated RNA, prepared essentially as described previously (Gough, N. M. *J. Mol. Biol.* 165: 683–699, 1983), was fractionated on 1% agarose gels containing 20 mM morpholinopropane sulfonic acid (MOPS), 5 mM sodium acetate, 1 mM EDTA (pH 7.0), plus 6% v/v formaldehyde, filters containing RNA were soaked in 2×SSC, containing 0.2% Ficoll, 0.2% polyvinyl- pyrollidone, 0.2% bovine serum albumin, 2 mM sodium pyrophosphate, 1 mM ATP, 50 μg/ml denatured salmon sperm DNA and 50 μg/ml *E. coli* tRNA, at 67° C. for several hours. Hybridization was in the same buffer plus 0.1% SDS at 67° C. The probe used to detect LIF transcripts consisted of an approx. 750 bp Eco RI - Hind III fragment containing the cDNA insert of pLIF7.2b subcloned in pSP65. This fragment contains not only the cDNA sequence but also G-C tails and approx. 150 bp of pJL3 vector sequence. Riboprobes of approx. $2 \times 10^9$ cpm/μg were derived by transcription of this SP6 subclone using reagents supplied by BRESA (Adelaide). The probe was included in hybridization at approx. $2 \times 10^7$ cpm/ml. Filters were washed extensively in 2×SSC, 2 mM EDTA, 0.1% SDS at 67° C. and finally in 0.2×SSC at 67° C. prior to autoradiography.

Such analysis revealed that LIF transcripts were present at low levels in a wide variety of haemopoietic cell lines and that there was considerable variation in the level of LIF mRNA in different batches of Krebs RNA. Two batches of Krebs ascites tumour cell RNA were selected for synthesis of two cDNA libraries. cDNA libraries were constructed using the reagents supplied by Amersham (Product numbers RPN.1256 and RPN. 1257) and using the manufacturer's instructions; the cloning vector was λGT10. Approximately $4 \times 10^5$ recombinant clones were obtained and screened by hybridization with an oligonucleotide corresponding to a sequence of 36 residues at the 3' end of the pLIF7.2b sequence: nucleotides 500–535 (inclusive) in FIG. 10.

Phage plaques representing the Krebs cDNA library were grown at a density of approx. 50,000 plaques per 10 cm petri dish, transferred in duplicate to nitrocellulose and treated using standard techniques (Maniatis, T. et al, *Molecular Cloning*, Cold Spring Harbor, 1982). Prior to hybridization, filters were incubated for several hours at 37° C. in 6×SSC (SSC=0.15M NaCl, 0.015M sodium citrate), 0.2% Ficoll, 0.2% polyvinyl-pyrollidone, 0.2% bovine serum albumin, 2 mM sodium pyrophosphate, 1 mM ATP, 50 mg/ml denatured salmon sperm DNA and 50 μ/ml *E. coli* tRNA. Hybridization was in the same solution containing 0.1% NP40, at 37° C. for 16–18 hours. The aforementioned oligonucleotide probe, radioactively labelled using [γ-$^{32}$P] ATP and polynucleotide kinase to a specific activity of approx. $10^9$ cpm/μg and separated from unincorporated label by ion exchange chromatography on a NACS column (Bethesda Research Laboratories), was included in the hybridization at a concentration of approx. 20 ng/ml. After hybridization, filters were extensively washed in 6×SSC, 0.1% sodium dodecyl sulphate at 60° C. One plaque representing clone λLIFNK1, positive on duplicate filters, was picked and rescreened at lower density, as before.

The cDNA insert of approx. 950 bp in λLIFNK1, which hybridized with the aforementioned oligonucleotide, was subcloned into a plasmid vector (pEMBL8+, Dente, L. et al, *Nucl. Acids Res.* 11: 1645–1655, 1983) to generate clone pLIFNK1. Nucleotide sequence analysis of the cDNA insert in pLIFNK1 was performed by the dideoxy chain termination method (Sanger, F. et al, *Proc. Natl. Acad. Sci. USA* 74: 5463–5467, 1977) using alkaline denatured double-stranded plasmid DNA as template (Chen, E. Y. and Seeburg, P. H., *DNA* 4: 165–170, 1985), a variety of oligonucleotides complementary both to regions of the vector flanking the cDNA and to sequences within the cDNA insert as primers, and using both the Klenow fragment of *E. coli* DNA polymerase and AMV reverse transcriptase as polymerases in the sequencing reactions. The nucleotide sequence of a portion of the cDNA insert in pLIFNK1 is shown in FIG. 11. The amino acid sequence specified by pLIFNK1 is identical at the C-terminus with the 9 amino acids predicted by direct amino acid sequencing to constitute the C-terminus of LIF, and confirms that Phe 187 is the C-terminal residue of LIF, since in the pLIFNK1 cDNA sequence the codon for this residue is immediately followed by an in-frame translational stop codon.

Step 2

Construction of a LIF Codon Region in a Yeast Expression Vector

Initial production of the protein encoded by the LIF cDNA clones was achieved in a eukaryotic system (yeast), so that the expressed product would be glycosylated, secreted and correctly folded. The expression vector used, YEpsec1 (Baldari, C. et al, *EMBO J.* 6: 229–234, 1987), provides an N-terminal leader sequence derived from the killer toxin gene of *Kluyveromyces lactis*, shown previously to direct the efficient secretion of interleukin 1 (Baldari, C. et al, *EMBO J.* 6: 229–234, 1987), transcribed from a galactose-inducible hybrid GAL-CYC promoter.

In order to express the protein encoded by pLIF7.2b in this vector, it was necessary to modify the cDNA in several ways (see FIG. 12). At the 5' end it was necessary not only to remove the few nucleotides specifying the partial mammalian leader sequence, but also to include an appropriate restriction endonuclease cleavage site (Bam HI) to allow insertion in-frame with the *K. lactis*. leader and retain an appropriate signal peptidase cleavage site (Gly-Ser). At the 3' end, two versions of the coding region for LIF were constructed. One version (LIFmut1) was constructed so that a stop codon immediately followed the last codon of pLIF7.2b (Gln 178). The other version (LIFmut2) was constructed to append a sequence encoding the 9 amino acid residues known to be missing from pLIF7.2b (see above), followed by an in-frame translational stop codon. An appropriate restriction endonuclease cleavage site (Hind III) completed both constructs. All of these modifications were achieved by oligonucleotide- mediated mutagenesis: The approx. 750 bp Eco RI - Hind III fragment carrying the 535 bp cDNA insert of pLIF7.2b, bounded by G-C tails and a portion of the pJL3 vector was subcloned into plasmid pEMBL8+ (Dente, L. et al, *Nucl. Acids Res.* 11: 1645–1655, 1983) and single-stranded DNA was prepared as described (Cesarini, G. and Murray, J. A. H. in Setlow, J. K. and Hollaender, A. (eds), *Genetic Engineering Principles and Methods*. Plenum Press, New York, Vol. 8, 1987 (in press)). In vitro mutagenesis was performed as described (Nisbet, I. T. and Beilharz, M. W. *Gene Anal. Techn.* 2: 23–29, 1985), using oligonucleotides of 35, 51 and 61 bases respectively, to modify the 5' end and the 3' end of the cDNA as outline above. Bam HI - Hind III fragments containing the modified LIF cDNA sequences were ligated into plasmid YEpsec1 and the nucleotide sequence of the inserts in the resulting recombinants was determined.

Step 3

Introduction of the YEpsec1/LIF Recombinants into Yeast Cells

*S. cerevisiae* strain GY41 (leu2, ura3 ade1 his4 met2 trp5 gall cir+; x 4003-5b from Yeast Genetic Stock Centre, Berkeley) was transformed by the polyethylene glycol method (Klebe, R. J. et al, *Gene* 25: 333–341, 1983). Transformants were selected and maintained on synthetic minimal medium (2% carbon source, 0.67% yeast nitrogen base (Difco) supplemented with 50 µg/ml of the required amino acids) under uracil deprivation. Expression of insert sequences in plasmid YEpsec1 was achieved by growing transformants in either non-selective complete medium (1% yeast extract, 2% peptone) or in synthetic minimal medium, each containing 2% galactose.

Step 4

Determination of the Biological Properties of Yeast-Derived LIF

Assays for differentiation-inducing activity and leukaemia-suppressive activity of yeast conditioned medium were performed in 1 ml cultures containing 300 M1 cells (provided by Dr. M. Hozumi, Saitama Cancer Research Centre, Japan) in Dulbecco's Modified Eagle's Medium with a final concentration of 20% foetal calf serum and 0.3% agar. Material to be assayed was added in serially diluted 0.1 ml volumes to the culture dish prior to the addition of the cell suspension in agar medium. Cultures were incubated for 7 days in a fully humidified atmosphere at 10% $CO_2$. Cultures were scored using a dissection microscope at ×35 magnification, scoring as differentiated any colonies with a corona of dispersed cells or composed wholly of dispersed cells. Morphological examination of colonies was performed by fixing the entire culture with 1 ml 2.5% glutaraldehyde then staining the dried cultures on microscope slides using acetylcholinesterase/Luxol Fast Blue/Haematoxylin.

Assays for colony stimulating activity were performed using 75,000 C57BL bone marrow cells as described previously (Metcalf, D. *The Hemopoietic Colony Stimulating Factors* Elsevier, Amsterdam, 1984). Assays for differentiation inducing activity on WEHI-3B D+ cells were performed as described previously (Nicola, N. et al, *J. Biol. Chem.* 258: 9017–9023, 1983).

Figures 13A, 13B:
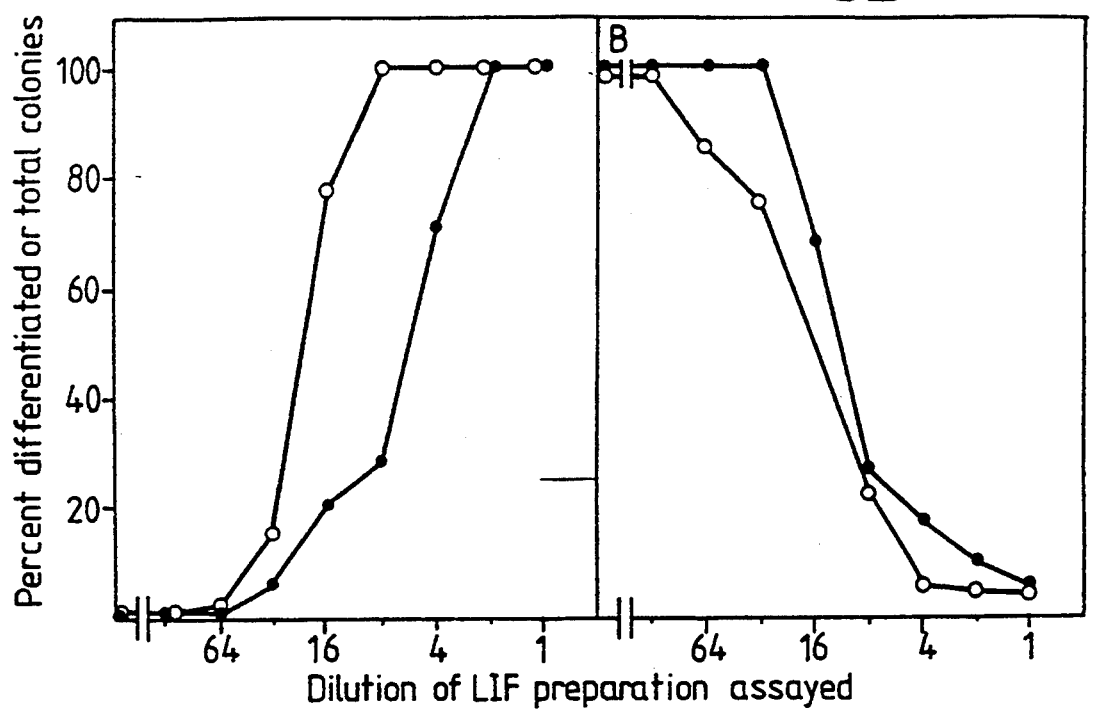
FIG. 13A and FIG. 13B depict the biological activity of yeast-derived recombinant LIF (solid circles) versus purified native LIF (open circles).

Medium from cultures of yeast containing the full-length coding region (LIFmut2), but not from cultures of non-transformed yeast, yeast containing the vector YEpsec1 alone, or yeast containing the incomplete coding region (LIFmut1), was able to induce typical macrophage differentiation in cultures of M1 colonies (FIG. 13A). As with purified native LIF, with increasing concentrations the yeast-derived material also progressively reduced the number and size of M1 colonies developing (FIG. 13B). Comparison with purified native LIF indicated that the yeast conditioned medium contained up to 16,000 Units/ml (approximately 130 ng/ml) of LIF. Yeast-derived LIF, like purified native LIF-A, failed to stimulate colony formation by normal granulocyte-macrophage progenitor cells or to induce differentiation in, or suppress proliferation, of WEHI-3B D+ leukaemic colonies.

Size fractionation on a Sephacryl S-200 column, indicated that yeast-derived LIF co-eluted with proteins of apparent molecular weight 67,000 to 150,000 Daltons, compared with 58,000 Daltons for LIF derived from Krebs cells.

The absence of LIF activity in medium conditioned by yeast containing an incomplete coding region (LIFmut1) suggests that the nine hydrophobic C-terminal residues missing from this construct might be required for LIF function. Whilst these residues might interact with the receptor, they may also constitute part of a hydrophobic core within the protein, and thus their absence may prevent proper folding. Alternatively they might in some way be required for efficient secretion of LIF.

Step 5

Receptor Binding Specificity of Yeast-Derived Murine LIF and Purified Native LIF-A from Krebs II Ascites Cell Conditioned Medium Purified murine LIF-A (Example 1) was iodinated as disclosed previously (Example 3). Peritoneal cells were harvested by lavage from mice in which a high level of macrophages had been induced in the peritoneal cavity with thioglycollate. These cells were washed and resuspended at $2.5 \times 10^6/50$ µl in Hepes-buffered RPMI medium containing 10% foetal calf serum. Cells in 50 µl aliquots were incubated with 200,000 cpm of $^{125}$I-LIF-A (10 µl, in the same medium) and 10 µl of control medium or serial two-fold dilutions of unlabelled pure murine LIF-A or yeast-derived murine LIF. At appropriate concentrations, supernatant from galactose-induced yeast containing the LIFmut2 construct (FIG. 12) competed for binding of $^{125}$I-LIF-A to its receptors on peritoneal cells while uninduced yeast supernatant did not (FIG. 14). The degree of competition was equal to that of authentic native LIF-A, indicating that the yeast-derived LIF-A contained all the information required for binding to LIF-A cellular receptors.

EXAMPLE 6

The following example sets out the steps used to express recombinant murine LIF in mammalian cells.

The accompanying FIG. 15 relates to step 1 of the method described below: The nucleotide sequence of the cDNA portion of clone pLIFNK3. The nucleotide sequence of the mRNA-synonymous strand is presented in the 5' to 3' orientation with the inferred amino acid sequence of LIF given above. The N-terminal amino acid residue previously determined is indicated as +1. The Eco R1 site at the 5' end of the cDNA and the Xba I site spanning the stop codon (used in inserting the LIF coding region into pMP-Zen in step 2) are indicated.

Step 1

Determination of the Amino Acid Sequence of the N-terminal Leader Sequence of Murine LIF The cDNA clones pLIF7.2b and pLIFNK1 (see above) contain incomplete copies of the LIF mRNA. Although they contain, together, the complete coding region for the mature portion of the LIF protein, they do not contain the complete hydrophobic leader sequence, required for secretion of LIF from mammalian cells.

In order to isolate a cDNA clone containing the region encoding the hydrophobic leader, a further $10^6$ cDNA clones constructed as above (Example 5), using the same batch of Krebs mRNA as a template, were screened (as above) using as probes two oligonucleotides corresponding to a sequence of 35 residues at the 5' end and 36 residues at the 3' end of the pLIF7.2b sequence (nucleotides 67–102 and 500–535, inclusive, in FIG. 10).

Two plaques representing clones λLIFNK2 and λLIFNK3, positive on duplicate filters were picked and rescreened at lower density, as previously. Since λLIFNK3 was shown to hybridize with each of the two oligonucleotides used, it was selected for further analysis.

The cDNA insert of approx. 1400 bp in λLIFNK3 was subcloned into the plasmid vector pEMBL 8+ (Dente, L., et. al., *Nucleic. Acids Res.* 11:1645–1655, 1983) to generate clone pLIFNK3. Nucleotide sequence analysis of the cDNA insert of pLIFNK3 was performed as for pLIF7.2b and pLIFNK1 (above).

The nucleotide sequence of the cDNA insert in pLIFNK3 is shown in FIG. 15, and indicates that pLIFNK3 contains a complete LIF coding region: there is an initiation codon (AUG) at position 23-25 in the pLIFNK3 sequence, preceding a sequence encoding a typical hydrophobic leader sequence of 24 amino acid residues. The coding region extends to the same translational stop codon as defined previously by pLIFNK1 (above).

Step 2

Introduction of a LIF Coding Region into a Mammalian Expression Vector

The mammalian expression vector chosen initially was the retroviral expression vector pMP-Zen. The vector is derived from the Moloney murine leukaemia virus-based vector pZIPNeo SV(X) (Cepko, C. L. et. al., *Cell* 37:1053–1062, 1984) by deletion of the neo$^R$ gene together with nearby SV40 and plasmid sequences, leaving an Xho I expression site. The 3' region of the vector is also modified to incorporate the enhancer from the long terminal repeat (LTR) of the myeloproliferative sarcoma virus (MPSV) (Bowtel, D. D. L. et. al., *Mol. Biol. Med.* 4:229–250, 1987). This vector was chosen, firstly since the LIF/PMP-Zen recombinant may be packaged into helper-free infectious retroviral particles by passage through ψ2 cells (Mann, R., et. al. *Cell*, 33:153–159, 1983). Such viral particles may then be used to efficiently introduce (by infection) the LIF/pMP-Zen recombinant into a wide variety of murine cell types (Mann, R. et. al. *Cell* 33:153–159, 1983). Secondly, this particular vector, which employs the MPSV LTRs for expression of the foreign coding region, has been shown to direct the efficient expression of certain other haemopoietic growth and differentiation factors including GM-CSF.

The segment of pLIFNK3 chosen for insertion into pMP-Zen extended from position 1 (an Eco R1 site) to position 630 (an Xba 1 site spanning the stop codon)—see FIG. 15. This segment was chosen since it contains little more than the coding region of pre-LIF and excludes all of the 3' untranslated region, which may contain sequences conferring mRNA instability (e.g. Shaw, G. and Kamen, R. *Cell* 46:659–667, 1986; Verma, I. M. and Sassone-Corsi, P., *Cell* 51: 513–514, 1987). In order to insert this segment into pMP-Zen, it was first inserted between the Eco R1 and Xba I sites of pIC20H (Marsh, J. L. et. al. *Gene* 32: 481–485, 1984) by standard techniques (Maniatis et. al., 1982, supra). The cDNA insert was then recovered from the polylinker of the pIC20H plasmid by Sal I plus Xho I digestion, thus generating a LIF cDNA fragment with cohesive ends appropriate for inserting into the Xho I cloning site of pMP-Zen. The insertion of the LIF cDNA fragment into pMP-Zen was achieved by standard techniques (Maniatis et. al., 1982, supra).

Step 3

Introduction of the pMP-Zen/LIF Recombinant into Murine Fibroblasts pMP-Zen/LIF DNA was introduced into ψ2 fibroblasts by electroporation (Potter et. al., *PNAS* 81:7161–7165, 1984). 30 µg pMP-Zen/LIF DNA plus 3 µg pSV2Neo DNA (Southern, P. J. and Berg, P. *J. Mol. App. Genet.* 1:327–341, 1982) were mixed with 1 × 10$^6$ ψ2 fibroblasts in 1 ml of DME/10% FCS (Dulbeccos modified Eagles medium containing 10% foetal calf serum) and subjected to a pulse of 500v at a capacitance of 25 µF (using a BioRad Gene-Pulser model No. 1652078). Transfectants were initially selected on the basis of resistance to the antibiotic G418 conferred by the pSV2Neo DNA. G418-resistant ψ2 cells were selected in 400 µg/ml G418 by standard procedures (Mann, R. et al, *Cell* 33: 153–159, 1983). Of 19 G418-resistant clones examined, 2 also contained the pMP-Zen/LIF construct as assessed by LIF activity detectable in ψ2 conditioned media.

Step 4

Determination of the Biological Properties of ψ2-Derived LIF

Assays for differentiation-inducing activity and leukaemia suppressive activity of conditioned medium from pMP-Zen/LIF containing ψ2 cells were performed as described previously. Medium from cultures of 10$^6$ ψ2 cells in 3 ml DME/10% FCS were assayed for differentiation-inducing activity. The results for two positive cultures are presented in the following table:

| Clone No. | M1 Differentiation-inducing Activity (Units/10$^6$ cells/ml C.M.) |
| --- | --- |
| ψ2-control | not detectable |
| ψ2-11a | >16,000 |
| ψ2-11d | >16,000 |

Thus, significant levels of biologically active, recombinant murine LIF can be produced in this expression system.

Step 5

Transmission of pMP-Zen/LIF Retrovirus from ψ2 Cells to Haemopoietic Cells

Infectious pMP-Zen/LIF retrovirus could be transferred from the parent ψ2 cell lines to haemopoietic cells of the line FDC-P1 (Dexter, T. M. et. al., *J. Exp. Med.* 152:1036–1047, 1980) by cocultivation. 10$^6$ ψ2 cells were mixed with 10$^6$ FDC-P1 cells in 10 ml DME/10% FCS containing the optimal concentration of WEHI-3BD− conditioned medium for growth of the FDC-P1 cells. Following 2 days incubation, the non-adherent FDC-P1 cells were removed, washed free from all adherent ψ2 cells and grown for 16 hours in 3 ml of the same medium. Conditioned medium was harvested and assayed for differentiation-inducing and leukaemia suppressive activity as described previously. The results are shown in the following table:

| FD Culture derived from Clone No. | M1 Differentiation-Inducing Activity (units/$10^6$ FDC-P1 cells) |
| --- | --- |
| ψ2-control | not detectable |
| ψ2-11a | approx. 3,000 |
| ψ2-11d - | approx. 1,500 |

Thus the ψ2 clones, ψ2-11a and ψ2-11d, are capable of transmitting biologically active pMP-Zen/LIF retrovirus to haemopoietic cells. These clones should therefore be applicable to the infection of normal murine haemopoietic progenitor cells which can be used to reconstitute the haemopoietic system of irradiated mice in order to study the effects of high level expression of native LIF on normal murine haemopoiesis, in a manner analogous to that used for Zen/GM-CSF viral infection.

EXAMPLE 7

The following sets out the steps used to express recombinant murine LIF in *E. coli* cells.

The accompanying FIG. 16 relates to step 1 of the method described below: The nucleotide sequence at the glutathione S-transferase/thrombin cleavage site/LIF junction in plasmid pGEX-2T/LIF, and the sequence at the junction of the encoded fusion protein. The C-terminus of the glutathione S-transferase, the thrombin cleavage site and the N-terminus of the murine LIF portions of the tripartite fusion protein, along with the nucleotide sequence encoding this amino acid sequence, are shown. The expected site of cleavage by thrombin is indicated by an arrow.

Step 1

Introduction of a LIF Coding Region into an *E. coli* Expression Vector

The expression vector used for expressing LIF in *E. coli* was pGEX-2T (Smith, D. B. and Johnson, K. S., *Gene* (in press), 1988), which directs the synthesis of foreign polypeptides as fusions with the C-terminus of Sj26, a 26 kD glutathione S-transferase (E.C. 2.5.1.18) encoded by the parasitic helminth *Schistosoma japonicum*. In the majority of cases, fusion proteins have been shown to be soluble in aqueous solutions and can be purified from crude bacterial lysates under non-denaturing conditions by affinity chromatography on immobilized glutathione. The particular vector pGEX-2T has been engineered so that the glutathione S-transferase carrier can be cleaved from the fusion protein by digestion with the site-specific protease thrombin.

The complete coding region of murine LIF, derived from plasmid pLIFmut2 (see Example 5 and FIG. 12 above) was introduced as a BamHI - EcoRI fragment into the multiple cloning site of pGEX-2T (Smith, D. B. and Johnson, K. S., supra), thus positioning the LIF coding region 3' of, and in the same translational reading frame as, that of the glutathione S-transferase and the thrombin cleavage site. Thus the LIF protein would be located C-terminal to these elements in a tripartite glutathione S-transferase/thrombin cleavage site/LIF fusion protein (see FIG. 16). Note that the position of the thrombin cleavage site is such that two amino acid residues (Gly-Ser) will be appended to the N-terminus of the LIF protein after thrombin cleavage. The construction of the aforementioned plasmid, pGEX-2T/LIF, was achieved by standard techniques, and the plasmid was introduced into *E. coli* NM522 (Gough, J. A. and Murray, N. M., *J. Mol. Biol.* 166: 1–19, 1983) by standard techniques.

Step 2

Expression and Purification of Glutathione S-Transferase/LIF Fusion Protein In order to induce the expression of the glutathione S-transferase/LIF fusion protein, 10 ml cultures of *E. coli* NM522 cells containing pGEX-2T/LIF were grown to logarithmic phase in Luria broth, and isopropyl β-D-thiogalactopyranoside added to a concentration of 0.1 mM. After a further 4 hours growth, during which time the glutathione S-transferase/LIF gene is expressed, the cells were harvested by centrifugation and resuspended in 1 ml mouse tonicity phosphate-buffered saline (MTPBS: 150 mM NaCl, 16 mM $Na_2HPO_4$, 4 mM $NaH_2PO_4$, pH7.3). Cells were lysed on ice by mild sonication and after adding Triton X-100 to 1%, cell debris was removed by centrifugation (10,000g, 5 min, 4° C.). The clarified supernatant was mixed at room temperature in a 50 ml polypropylene tube on a rotating platform with 200 μl 50% glutathione-agarose beads (sulphur linkage, Sigma). (Before use, beads were pre-swollen in MTPBS, washed twice in the same buffer and stored in MTPBS at 4° C. as a 50% solution v/v). After absorption (5 min.), beads were collected by centrifugation (500g, 1 min) and washed three times in MTPBS/Triton X-100. The glutathione S-transferase/LIF fusion protein was then eluted by competition with free glutathione: beads were incubated with 100 μl 50 mM Tris. HCl, 5 mM reduced glutathione (pH 7.5) for 2 min at room temperature and the beads removed by centrifugation. The elution step was performed twice, and the two 100 μl aliquots of eluate pooled.

100 μl of the glutathione S-transferase/LIF fusion protein was treated with thrombin as described (Smith, D. B. and Johnson, K. S., supra).

1 μl aliquots of the uncleaved and thrombin-cleaved glutathione S-transferase LIF fusion proteins were electrophoresed on a Pharmacia Phast Gel (8–25% polyacrylamide gradient gel). After staining with Coomassie Blue, a single major protein species of relative molecular weight ~46 kDa was revealed in the uncleaved preparation, and in the thrombin-cleaved preparation two major bands of ~26 kDa and ~20 kDa (corresponding to the expected sizes of the fusion protein (46 kDa), the glutathione S-transferase (26 kDa) and the LIF proteins (20 kDa) respectively). By estimating the mass of the Coomassie-stained bands on this gel, the yield of glutathione S-transferase/LIF protein from the original 10 ml *E. coli* culture was estimated to be ~1.5 μg.

Assays for differentiation-inducing activity and leukaemia-suppressive activity of both the glutathione S-transferase/LIF fusion protein and the thrombin cleaved LIF preparation, were performed using murine M1 cells (as described previously). Both preparations of LIF were determined to be biologically active, with specific activities in excess of $7 \times 10^6$ units/mg.

EXAMPLE 8

The following sets out the steps used to determine whether the murine genome contains any other genes closely related to the gene encoding the sequence present in clone pLIF7.2b (Example 4) and the derivation of a map of the location of restriction endonuclease cleavage sites around the LIF gene.

Figure 17:
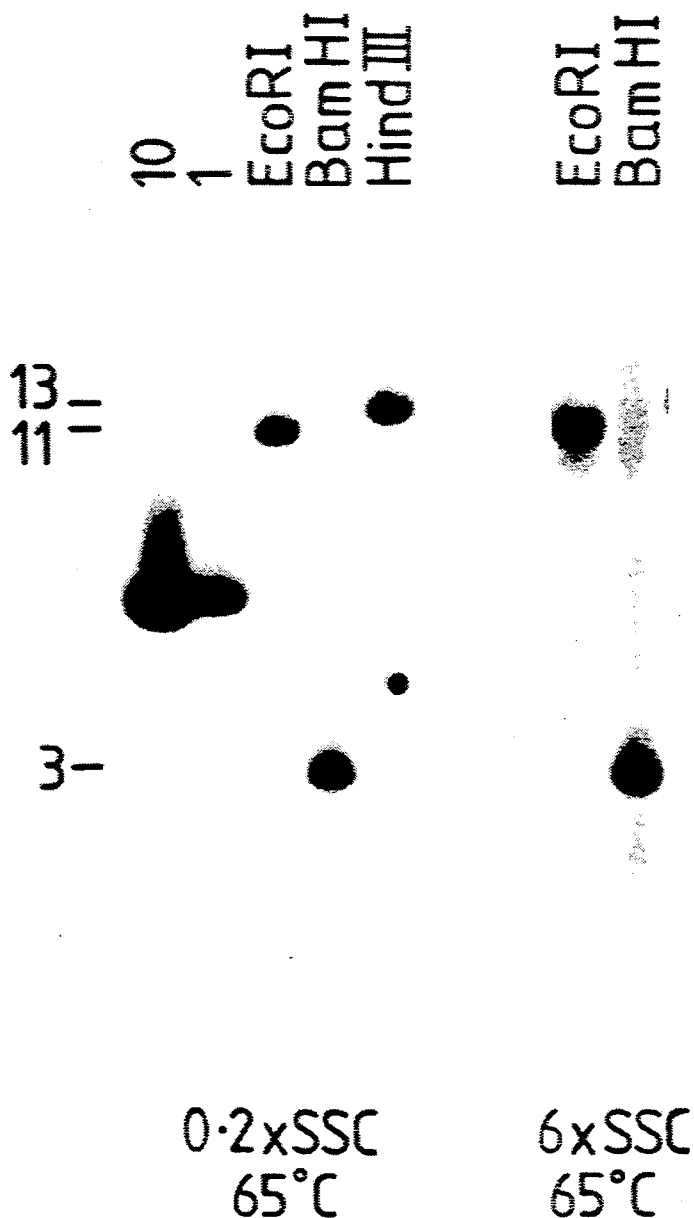
FIG. 17 shows the hybridization of mouse DNA with a pLIF 7.2b derived probe at low and high stringency.

The accompanying Figures relate to various steps of the method described below:

FIG. 17: relates to step 1: hybridization of mouse DNA with a pLIF7.2b-derived probe under high and low stringency conditions. BALB/c liver DNA digested with the indicated restriction enzymes was probed for LIF gene sequences as described in Example 8, step 1. In the left hand panel, hybridization was at 65° C. in 2×SSC, and final washing at 65° C. in 0.2×SSC. In the right hand panel, hybridization and washing were both in 6×SSC at 65° C. In the left hand panel, linear pLIF7.2b plasmid DNA (5.6 kb) was included at an amount equivalent to 10 and 1 copies per haploid mouse genome (400 pg and 40 pg respectively) assuming a molecular weight for the haploid mouse genome of $3 \times 10^9$ bp (Laird, C. D. *Chromosoma*, 32: 378–406, 1971). The sizes of the hybridizing genomic fragments are indicated.

Figure 18:
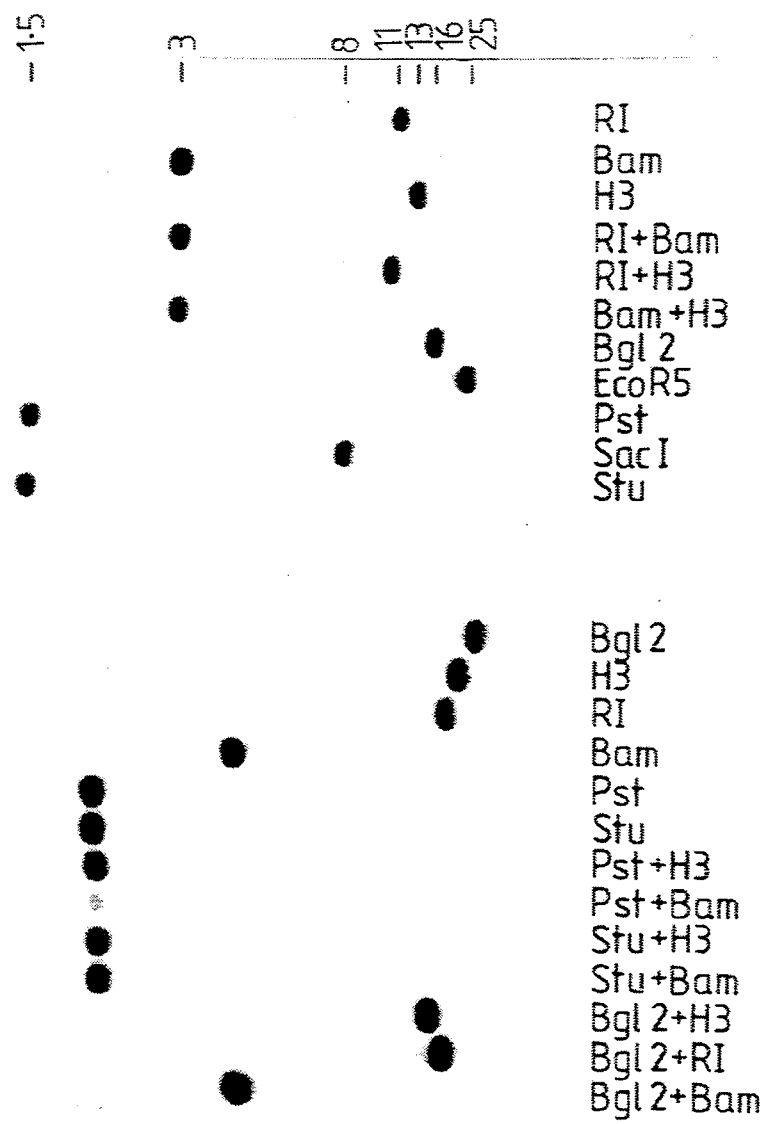
FIG. 18 shows the hybridization of differently obtained fragments of mouse DNA with pLIF 7.2b-derived probe at high stringency.

FIG. 18: relates to step 2: Hybridization of mouse DNA cleaved with various restriction endonucleases, singly and in pair-wise combinations, with a mouse LIF probe. Digested DNAs were electrophoresed on 0.8% agarose gels and hybridized with the pLIF7.2b cDNA fragment as described in Example 8, step 1, under high stringency conditions.

Figure 19:
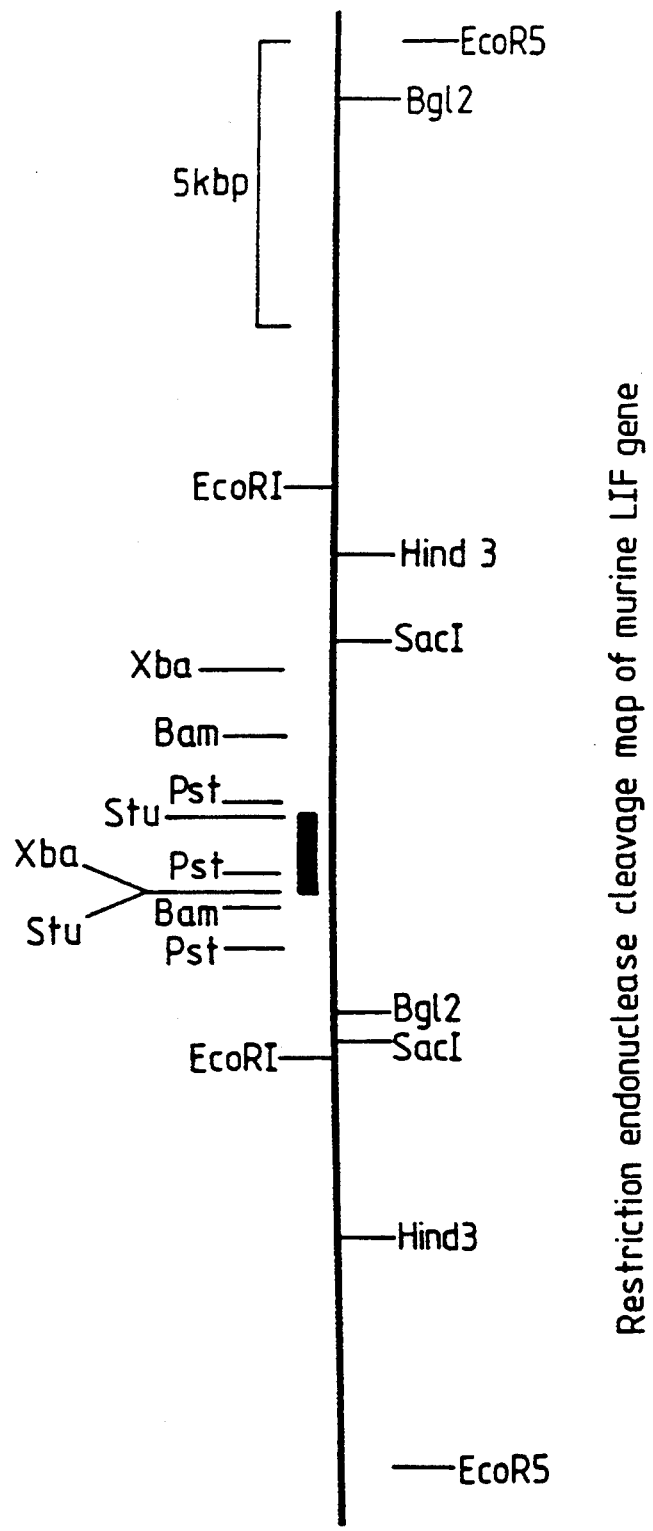
FIG. 19 provides a cleavage map of the murine LIF gene.

FIG. 19: relates to step 2: Restriction endonuclease cleavage map of the murine LIF gene. The region of chromosomal DNA containing sequences corresponding to the cDNA clone pLIF7.2b is indicated by a box. The restriction sites given above (Eco R5) and below (Xba I, Bam HI, Pst I and Stu I) the central line have not been oriented with respect to the central line. The relative location of sites within the complex below the line is as indicated.

Figure 20:
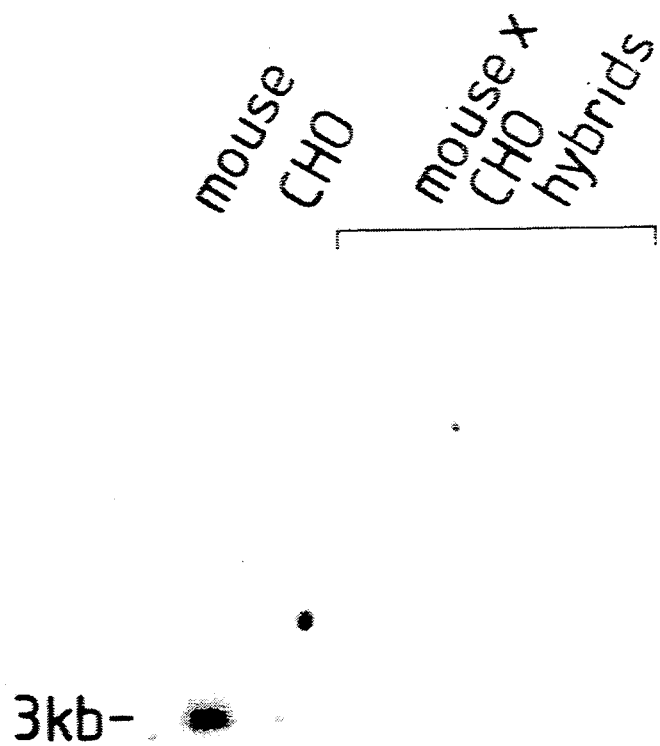
FIG. 20 relates to the chromosomal assignment of the murine LIF gene.

FIG. 20: relates to step 3: chromosomal assignment of the murine LIF gene. In lane 1 BALB/c mouse embryo DNA was electrophoresed, in lane 2, DNA from Chinese hamster ovary cells and in lanes 3–8 DNA from the hybrid clones I-18A HAT, I-18A-2a-8AG; EBS 58; EBS 11; EBS 4; and I-13A-1a-8AG (Cory, S. et al, (*EMBO J.* 2: 213–216, 1983). The murine chromosome content of these hybrids is given in Cory, S. et al, (*EMBO J.* 2: 213–216, 1983). All DNAs were digested with Bam HI. The position of the 3 kbp Bam HI fragment bearing the murine LIF gene is indicated.

Step 1

Determination of the Number of LIF-Related Genes in the Murine Genome

In view of the data (Example 1) that medium conditioned by Krebs II cells contains two biochemically separable but functionally similar factors capable of inducing the differentiation of M1 cells (LIF-A and LIF-B) we wished to determine how many genes there are in the murine genome related to the species we have purified and cloned. Southern blots of murine genomic DNA digested with various restriction endonucleases were therefore hybridized with a probe derived from pLIF7.2b under conditions of both high and low stringency.

20 μg aliquots of high molecular weight genomic DNA from BALB/c mouse livers were digested to completion with various restriction endonucleases, fractionated by electrophoresis in 0.8% agarose gels and transferred to nitrocellulose. Prior to hybridization, filters were incubated for several hours at 65° C. in either 6×SSC (low stringency) or 2×SSC (high stringency) (SSC=0.15M NaCl, 0.015M sodium citrate), 0.2% Ficoll, 0.2% polyvinyl-pyrollidone, 0.2% bovine serum albumin, 2 mm sodium pyrophosphate, 1 mM ATP, 50 μg/ml denatured salmon sperm DNA and 50 μg/ml *E. coli* tRNA. Hybridization was in the same solution containing 0.1% SDS, at 65° C. for 16–18 hours. Filters were then washed in either 6×SSC, 0.1% SDS at 65° C. (low stringency) or in 2×SSC, 0.1% SDS at 65° C., followed by 0.2×SSC, 65° C. (high stringency) as detailed in the legend to FIG. 17. The hybridization probe used was as previously disclosed the approx. 750 bp Eco RI - Hind III fragment spanning the cDNA insert of pLIF7.2b radiolabelled to a specific activity of approx. $4 \times 10^8$ cpm/μg by nick-translation and included in the hybridization at a concentration of approx. $2 \times 10^7$ cpm/ml.

In mouse liver DNA (FIG. 17) as well as in DNA from Krebs II cells, LB3 T cells and WEHI265 monocytic cells (not shown) the LIF probe detected unique Eco RI, Bam HI, and Hind III fragments of approximately 11, 3 and 13 kbp respectively. The same pattern of hybridization was evident at both high (0.2×SSC, 65° C.) and low stringency (6×SSC, 65° C.) (FIG. 17); under low stringency hybridization and washing conditions no additional bands were evident. Similarly, unique hybridizing fragments were also detected in Pst I, Stu I, Sac I, Eco R5 and BgI II-digested genomic DNA (FIG. 17). Moreover, in the experiment illustrated in FIG. 16, pLIF7.2b plasmid DNA was included at a concentration equivalent to 10 and 1 copies per haploid mouse genome (tracks 1 and 2); the hybridization intensity of the genomic LIF sequences was not significantly different from the intensity of the unique gene standard (track 2).

Taken together, the foregoing data indicate that the LIF gene is unique in the murine genome, with no close relatives. Thus the two species of LIF are not likely to be products of different genes, but rather are more likely to represent post-transcriptional or post-translational variants of the same gene product.

Step 2

Derivation of a Restriction Endonuclease Cleavage Map of the Murine LIF Gene In order to determine the disposition of restriction endonuclease cleavage sites in and around the murine LIF gene, and thus provide a molecular fingerprint of this gene, DNA from mouse livers or from Krebs ascites tumour cells was digested with various restriction endonucleases and subjected to Southern blot analysis described in Step 1 (under high stringency hybridization and washing conditions). Examples of such experiments are shown in FIG. 18. Analysis of the size of the digestion products enables one to generate a map of the location of each cleavage site around the LIF gene (FIG. 19).

Step 3

Chromosome Assignment of the Murine LIF Gene

To determine the chromosome on which the mouse LIF gene is located, DNA was examined from six mouse-Chinese hamster ovary somatic cell hybrid cell lines which retain various mouse chromosomes (Cory, S. et al, *EMBO J.* 2: 213-216, 1983; Francke, U. et al, *Cytogenet. Cell. Genet.* 19: 57-84, 1977). Southern blot analysis performed as described in Step 1 (using high stringency hybridization and washing conditions) indicated that the 3 kbp Bam HI fragment containing the murine LIF gene was absent from all of the hybrids (FIG. 20). Since chromosome 11 is the only mouse chromosome not retained in any of these lines (Cory, S. et al, *EMBO J.* 2: 213-216, 1983), a characteristic of mouse-Chinese hamster hybrids (Francke, U. et al, *Cytogenet. Cell. Genet.* 19: 57-84, 1977), it is likely that the LIF gene is on this chromosome. On the same basis, the murine GM-CSF gene (Barlow, D. P. et al, *EMBO J.* 6: 617-623, 1987) and Multi-CSF gene (Ihle, J. N. and Kozak, C. A., *National Cancer Institute, Frederick, Cancer Research Facility, Annual Report,* 1984) have also been assigned to chromosome 11, an assignment confirmed by genetic linkage studies (Barlow, D. P. et al, *EMBO J.* 6: 617-623, 1987).

EXAMPLE 9

The following example sets out the steps used to establish conditions under which the cloned murine LIF cDNA can be used to identify by hybridization a human gene or mRNA or recombinant DNA clones containing human LIF-encoding sequences.

The accompanying Figure (FIG. 21) relates to Step 2 of the method described below: hybridization of $^{32}$P-labelled fragment of cDNA from clone pLIF7.2b under various conditions to genomic DNA of both mouse and human origin. In each case, track 1 contains 15 μg murine (LB3) DNA and track 2 and 3 contain 15 μg human DNA (from the cell lines Raji or Ramos, respectively). The hybridization and washing conditions applied to each filter are described in Step 2. The approximately 10 kbp Eco RI fragment containing the murine LIF gene, and the approximately 9 kbp Eco RI fragment containing the human homologue, are arrowed. Molecular weight standards are given at the left. Two different autoradiographic exposures (16 hours and 62 hours) age shown.

Step 1

Preparation and Radioactive Labelling of a Fragment of cDNA from pLIF7.2b pLIF7.2b plasmid DNA was amplified by growth in *E. coli* MC1061 (Casadaban, M. and Cohen, S., *J. Mol. Biol.* 138:179-207, 1980), extracted from the *E. coli* cells by standard procedures (Maniatis, J. et al, *Molecular Cloning,* Cold Spring Harbor, New York, 1982) and purified by CsCl-gradient centrifugations. pLIF7.2b plasmid DNA so purified was cleaved with the restriction endonucleases Eco RI and Hind III to release a cDNA-containing fragment of ~770 bp from the vector (pJL3), which was resolved from vector sequences by electrophoresis through a 1.5% agarose gel.

200 ng of pLIF7.2 cDNA fragment thus purified was radioactively labelled to a specific activity of approximately $3 \times 10^8$ cpm/μg by nick-translation (Rigby, P. W. J., Dieckmann, M., Rhodes, C. and Berg, P., *J. Mol. Biol.* 113:237-251, 1977) in a reaction containing 100 μCi [$\alpha^{32}$P]-dATP. The radioactively labelled cDNA fragment was purified from unincorporated label by precipitation in the presence of 1M sodium perchlorate and 33% isopropanol.

Step 2

Hybridization of Southern Blots of Mouse and Human Genomic DNA with a pLIF7.2b cDNA Probe High molecular weight genomic DNA (15 μg) from the murine T cell line LB3 (lane 1) and from two human B cell lines (Raji and Ramos; lanes 2 and 3) cleaved with the restriction endonuclease Eco RI was electrophoresed through a 0.8% agarose gel and transferred to nitrocellulose using standard techniques (Southern, E. M., *J. Mol. Biol.* 98:503-517, 1975). Five identical Southern blots were prepared containing each of these three DNAs. Before hybridization, filters were incubated for several hours at 55° C. in either 0.9M NaCl, 0.09M sodium citrate, 0.2% Ficoll, 0.2% polyvinylpyrollidone, 0.2% bovine serum albumin, 50 μg/ml heat denatured salmon sperm DNA, 50 μg/ml *E. coli* tRNA, 0.1 mM ATP and 2 mM sodium pyrophosphate (filters a, b, c, d) or in 0.3M NaCl, 0.03M sodium citrate, with the same additional components (filter e). Hybridization with the $^{32}$P-labelled pLIF7.2b cDNA prepared in Step 1 was performed in the same solutions as the prehybridization, containing in addition 0.1% sodium dodecyl sulphate, at 55° C. (filters a, b, c), or 65° C. (filters d, e) for 16 hours. The $^{32}$P-labelled cDNA was denatured by boiling prior to hybridization and was included in the hybridization reaction at ~$10^7$ cpm/ml.

Figure 21:
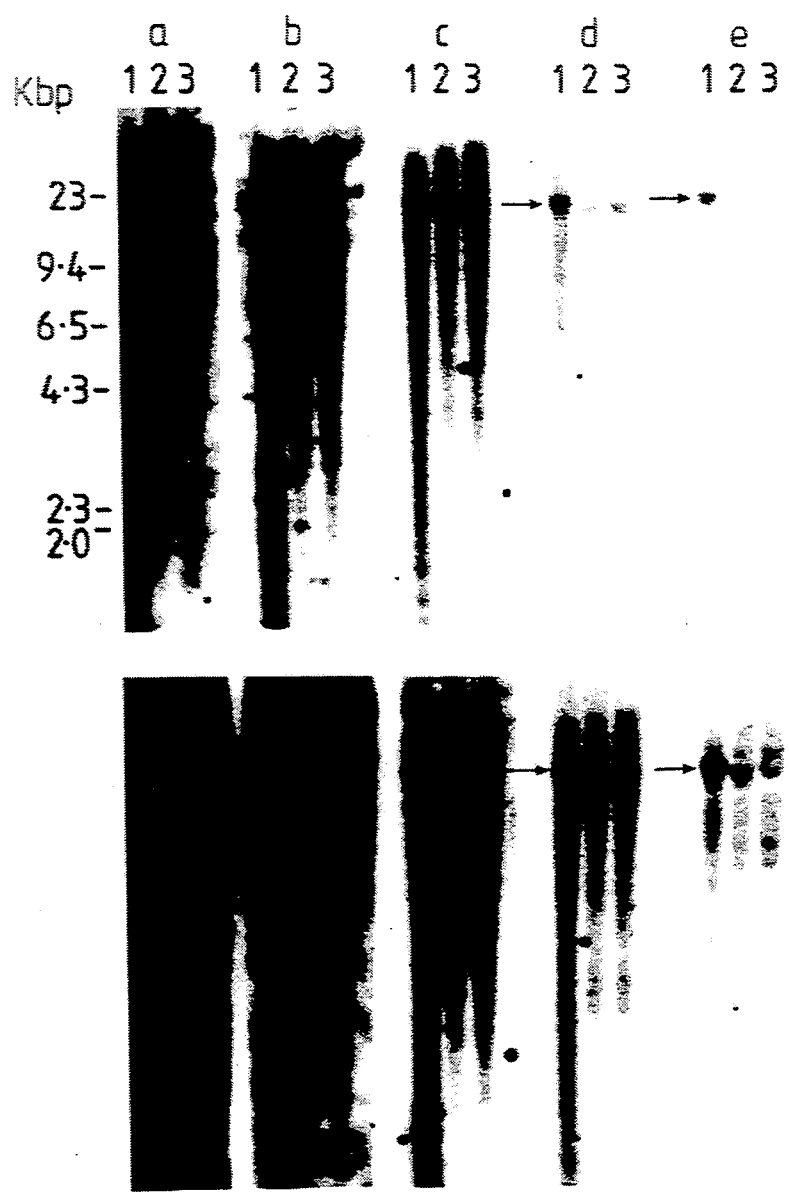
FIG. 21 shows the hybridization of human and mouse genomic DNA to a pLIF 7.2b-derived probe.

After hybridization the filters were washed in either 0.9M NaCl, 0.09M sodium citrate, 0.1% sodium dodecyl sulphate at 55° C. (filter a) 60° C. (filter b) or 65° C. (filters c, d) or in 0.3M NaCl, 0.03M sodium citrate, 0.1% sodium dodecyl sulphate at 65° C. (filter e). After exhaustive washing, filters were autoradiographed at −70° C. using Kodak XAR-5 film and two intensifying screens. FIG. 21 shows the results of such an experiment, in which two of the hybridization/washing regimes described (filters d and e) allowed both the murine LIF gene (present on an approximately 10 kbp Eco RI fragment) and the human LIF gene (present on an approximately 9 kbp Eco RI fragment) to be detected above residual background non-specific hybridization. All other conditions tested gave rise to an unacceptably high level of background hybridization (filters, a, b, c).

EXAMPLE 10

The following example sets out the steps used to obtain a cloned human gene homologous to murine LIF.

Figure 22:
FIG. 22 shows hybridization of a mouse LIF cDNA probe to variously obtained fragments of human genomic DNA.

The accompanying Figures relate to various steps of the method described below. In the Figures:

FIG. 22: relates to step 1 of the cloning of the human LIF gene: Detection of the LIF gene by Southern blot hybridization using a mouse LIF cDNA probe. Genomic DNA from the human cell line RAMOS was digested with the indicated restriction endonucleases and hybridized under the conditions described in Example 19, step 1, with a mouse cDNA fragment derived from pLIF7.2b.

Figure 23:
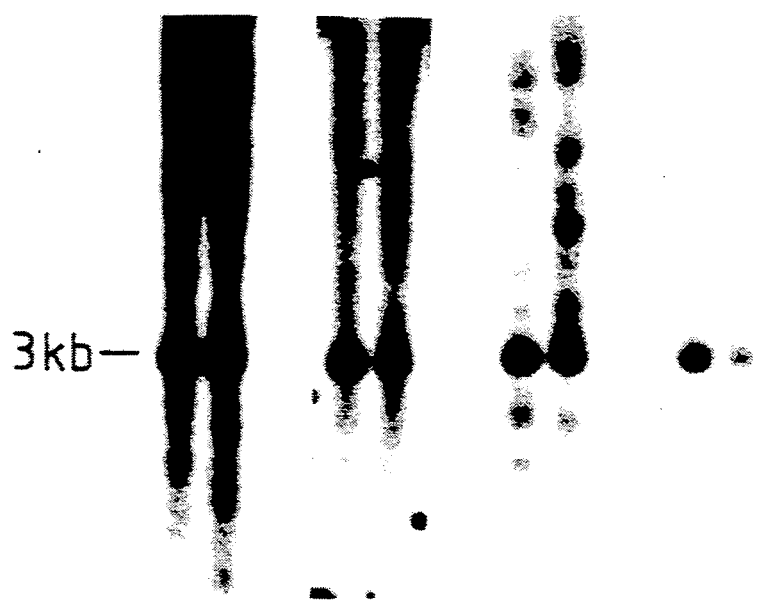
FIG. 23 shows hybridization of a mass LIF cDNA probe to human or mouse genomic DNA under various hybridization conditions.

FIG. 23: relates to step 1 of the cloning of the human LIF gene: detection of the LIF gene by Southern blot hybridization using a mouse LIF cDNA probe under a variety of hybridization conditions. Genomic DNA from the human cell line RAMOS (H) or mouse liver DNA (M) digested with the restriction endonuclease Bam HI were hybridized with a murine LIF cDNA probe (pLIF7.2b) under a variety of conditions of hybridization and washing. The temperatures and concentrations of SSC used for hybridization are indicated on the top line and the conditions of washing on the second line (see Example 10, step 1).

Figure 24:
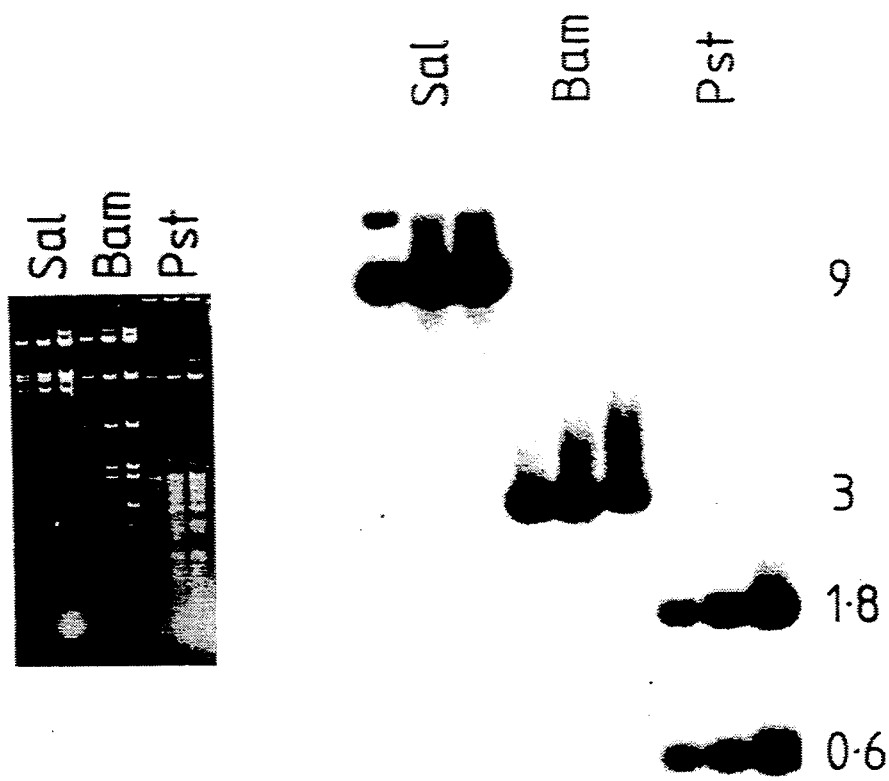
FIG. 24 studies the cleavage patterns of three candidate LIF gene clones.

FIG. 24: relates to step 2 of the cloning of the human LIF gene: restriction endonuclease cleavage of three candidate LIF gene clones. 1 µg of DNA from λ phage of the clones λHGLIF1, λHGLIF2 and λHGLIF3 was digested with Sal I, Bam HI or Pst I, electrophoresed on an 0.8% agarose gel (left hand panel), transferred to nitrocellulose and hybridized (as disclosed previously) with pLIF7.2 cDNA. The approximate sizes of the hybridizing fragments are indicated.

FIG. 25: relates to step 3 of the cloning of the human LIF gene: The nucleotide sequence of the mRNA-synonymous strand of a 1.3 kbp segment of λHGLIF1 spanning the human LIF gene (H) is presented in a 5' to 3' orientation. The corresponding nucleotide sequence of the murine LIF mRNA (M) derived from cDNA clones pLIF7.2b, pLIFNK1 and pLIFNK3 is aligned beneath the human gene and given in lower case letters. Identities between the mouse and human sequences are indicated with asterisks. The presumed N-terminal residue of mature human LIF, by analogy with mouse LIF, is designated as +1.

FIG. 26: relates to step 3 of the cloning of the human LIF gene: amino acid sequence of human LIF and comparison with mouse LIF. The amino acid sequence of mature murine LIF (M) as determined by direct amino acid sequencing, and analysis of the cDNA clones pLIF7.2b, pLIFNK1 and pLIFNK3 is listed on the top line, with the corresponding sequence of human LIF (H), as deduced from the sequence of λHGLIF1, listed below. Identities are indicated with [asterisks].

Figure 27:
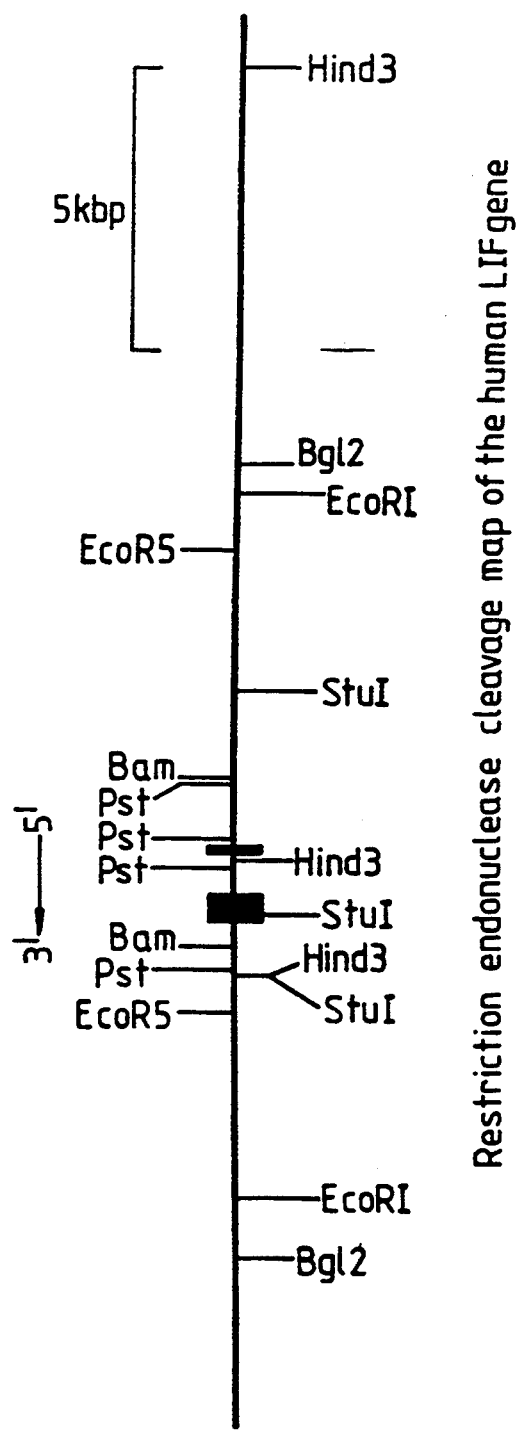
FIG. 27 provides a cleavage map of the human LIF gene.

FIG. 27: relates to step 4 of the cloning of the human LIF gene: restriction endonuclease cleavage map of the human LIF gene. The exons of the human gene homologous with pLIF7.2b (FIG. 25) are indicated as boxes. The direction of transcription of the gene is indicated by the arrow below the line.

Step 1

Detection of the Human LIF Gene with a Mouse Probe

A method has been previously disclosed for using a radioactively labelled fragment of the mouse LIF cDNA clone pLIF7.2b as a hybridization probe to detect the human LIF gene. FIG. 22 demonstrates that this method allows the human LIF gene to be detected in human genomic DNA digested with a variety of restriction endonucleases. Analyses such as this, and other gels not shown, revealed the sizes of DNA fragments generated by a variety of restriction endonucleases on which the human LIF gene is located. Such data is of importance in subsequent steps of this example, not only to establish conditions under which the mouse probe can be used as a hybridization probe to detect the human, but also to provide diagnostic restriction mapping data to aid in identifying human genomic LIF clones.

A high degree of homology between the mouse and human LIF sequences was apparent when mouse and human genomic DNA digested with Bam HI was hybridized with a mouse LIF cDNA probe under a variety of conditions of hybridization and washing (FIG. 23). As the stringency of hybridization and washing was raised, so the background smear was reduced, revealing a unique fragment of ~3 kbp hybridizing with the mouse probe. Significantly, the human gene retained substantial hybridization even at 65° C. in 0.2×SSC.

Step 2

Screening of a Human Genomic Library and Isolation of a Clone Containing the LIF Gene A library of human genomic DNA, partially digested with Sau 3A and ligated into the lambda phage cloning vector EMBL3A, was screened for LIF gene-containing clones by hybridization with the mouse cDNA as a probe. The fragment of LIF cDNA was radioactively labelled and the conditions of hybridization were as disclosed previously (Example 4). Briefly, phage plaques representing the genomic library were grown at a density of ~50,000 plaques per 10 cm petri dish and transferred to nitrocellulose as described (Maniatis, T. et al, Molecular Cloning, Cold Spring Harbor, 1982). Prior to hybridization, filters were incubated for several hours at 65° C. in 6×SSC (SSC=0.15M NaCl, 0.015M sodium citrate), 0.2% Ficoll, 0.2% polyvinyl-pyrollidone, 0.2% bovine serum albumin, 2 mM sodium pyrophosphate, 1 mM ATP, 50 µg/ml denatured salmon sperm DNA and 50 µg/ml E. coli tRNA. Hybridization as in the same solution containing 0.1% SDS, at 65° C. for 16–18 hours. The LIF cDNA fragment, radioactively labelled by nick-translation using $[\alpha^{32}P]$ dATP to a specific activity of $\sim 2 \times 10^8$ cpm/µg was included in the hybridization at a concentration of $\sim 2 \times 10^6$ cpm/ml. After hybridization, filters were extensively washed in 6×SSC, 0.1% sodium dodecyl sulphate at 65° C. and then autoradiographed. Plaques positive on duplicate filters were picked and rescreened at lower density, as before.

Three clones were thus identified and purified: λHGLIF1, 2 and 3. In order to determine the relationship between these clones and to determine which, if any, contain the human LIF gene, DNA was prepared from each clone and digested with these restriction endonucleases: Sal I which liberates the entire segment of cloned genomic DNA and Bam HI and Pst I which cleave in and around the LIF gene to generate characteristic fragments of ~3 kbp and 1.8 kbp and 0.6 kbp respectively (as determined above). After digestion of the recombinant phage DNAs and resolution by electrophoresis on agarose gels (FIG. 24, left hand panel), the DNA was transferred to nitrocellulose and hybridized with the mouse LIF cDNA probe (under the conditions outlined above) to reveal the fragments containing the LIF gene (FIG. 24, right hand panel). This analysis revealed that (a) all three clones appeared to be identical;

(b) all contain an ~9 kbp segment of genomic DNA containing a region homologous with the mouse LIF probe;

(c) the region of homology with the mouse cDNA is present on a 3 kbp Bam HI fragment and on 1.8 and 0.6 kbp Pst I fragments, characteristics of the human LIF gene (see above). Thus it was concluded that all three clones contain a segment of chromosomal DNA encompassing the human LIF gene.

Step 3

Determination of the Nucleotide Sequence of the Human LIF Gene

The ~3 kbp Bam HI fragment of λHGLIF1 shown above to hybridize with the mouse LIF cDNA probe was recloned into the plasmid vector pEMBL8+, giving rise to clone pHGLIFBam1, and subjected to nucleotide sequence analysis. Nucleotide sequencing was performed by the dideoxy chain termination method (Sanger, F. et al, *Pro. Natl. Acad. Sci. USA.* 74: 5463-5467, 1977) using alkaline denatured double-stranded plasmid DNA as template, a variety of oligonucleotides complementary to sequences within the gene as primers, and using both the Klenow fragment of *E. coli* DNA polymerase I and the arian myeloblastosis virus reverse transcriptase as polymerases in the sequencing reactions.

The entire nucleotide sequence of the Bam HI fragment spanning the LIF gene (2840 bp) was determined, of which 1297 bp is shown in FIG. 25. Alignment of this sequence with the murine LIF mRNA sequence revealed that the sequences encoding the mature human LIF protein are present on two exons separated by an intron of 693 bp (FIG. 25). For the region encoding the mature protein there is a high degree of homology between the two species at both the nucleotide and the amino acid sequence level. Within exon 1 there is 88% nucleic acid sequence homology (114/129 residues compared) and 91% amino acid sequence homology (39/43) for the region encoding the mature protein (position 58-186). Exon 2 is somewhat less homologous, 77% at the nucleotide level (318/411) and 74% at the amino acid level (101/136) within the coding region. Considering the mature protein as a whole, mouse and human LIF sequences determined here are identical at 140 of 179 positions (78%) with no insertions or deletions (FIG. 26). Moreover, many of the differences are highly conservative substitutions (Lys :Arg, Glu:Asp and Leu :Val :Ala).

5' of the codon for the N-terminal proline residue of mature LIF, (position 58 in FIG. 25) the human gene is homologous with the murine LIF mRNA sequence through a region encoding most of the hydrophobic leader. However, the entire leader is not encoded on this exon, since the mRNA and gene sequences diverge at a typical RNA splice site (TCCCCAG) (Mount, S. M., *Nucleic Acids Res.* 10:459-472, 1982). The exon specifying the 5' untranslated region and the first residues of the leader is not present within 1097 bp 5' of this splice site. In the mouse LIF gene, the exon specifying the first 6 amino acid residues of the hydrophobic leader is located ~1.5 kbp 5' of the analogous splice site.

Step. 4

Derivation of a Restriction Endonuclease Cleavage Map of the Human LIF Gene In order to determine the disposition of the restriction endonuclease cleavage sites in and around the human LIF gene, and thus provide a molecular fingerprint of this gene, human genomic DNA (from the RAMOS cell line) was digested with various restriction endonucleases singly and in pair-wise combinations and subject to Southern blot analysis as described in Example 8, except that the probe used was the 3 kbp Bam HI fragment derived from pHGLIFBam1 described in Step 3 above and radiolabelled by nick-translation. Analysis of the data so-derived (not shown), as well as that shown in FIG. 22 and derived from analysis of λHGLIF1 and pHGLIFBam1, gave rise to the restriction endonuclease cleavage map shown in FIG. 27.

EXAMPLE 11

The following example details modifications made to the cloned human LIF gene in order to allow expression in yeast cells and determination of the biological and biochemical properties of the recombinant human LIF so derived.

Figures 16, 28:
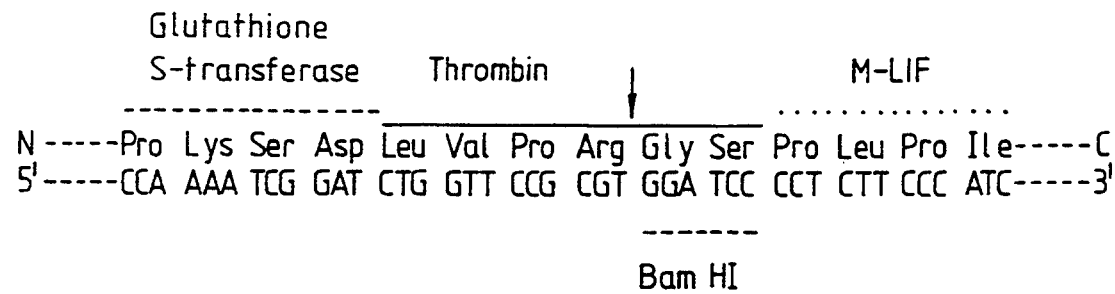
FIG. 16 depicts the cleavage site of the glutathione S-transferase/thrombin/M-LIF fusion protein.
FIG. 28 shows how the human LIF cDNA was modified for expression in YEpsec1.

In the Figures,

FIG. 28: relates to step 1: oligonucleotides used to modify the human LIF gene for incorporation into YEpsec1. Oligonucleotide (a) corresponds to the 5' end of the coding region (residues 31 to 69 in FIG. 25). Oligonucleotide (b) corresponds to the middle of the coding region (residues 163 to 186 and 880 to 903 in FIG. 25). The portion of this oligonucleotide complementary to exon 1 is underlined with dashes, and that complementary to exon 2 with dots. Oligonucleotide (c) corresponds to the 3' end of the coding region (from position 1279 in FIG. 25). Oligonucleotides (a) and (b) introduce the indicated restriction endonuclease cleavage sites.

FIG. 29: relates to step 1: nucleotide sequence of, and amino acid sequence encoded by, the synthetic human LIF cDNA derived by mutagene sis of the cloned human LIF gene. The Bam HI and Hind III cleavage sites introduced by oligonucleotides (a) and (c) (FIG. 28) are indicated. The presumed N-terminal amino acid of mature LIF (by analogy with the mouse) is designated as +1.

Figure 30:
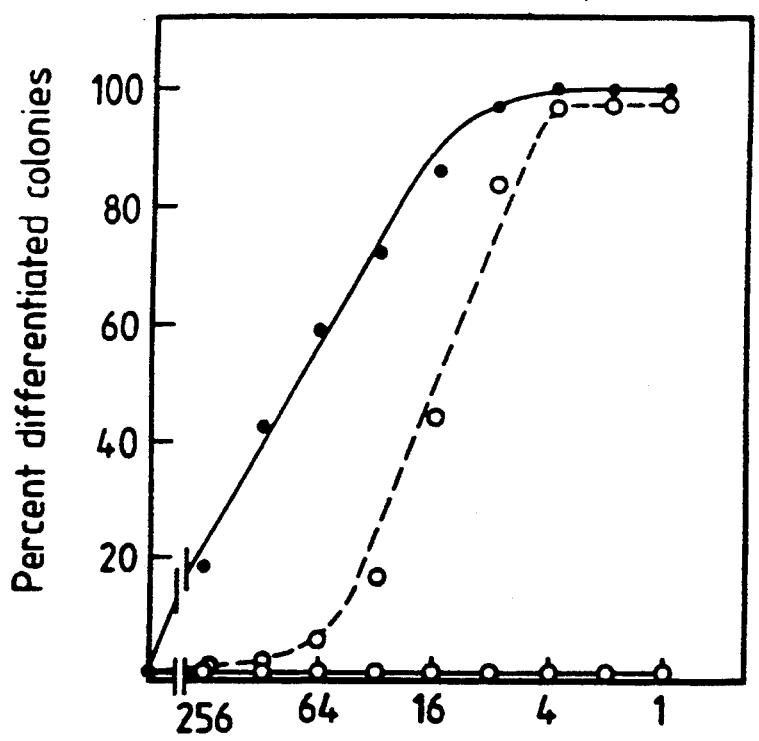
FIG. 30 shows induction of differentiation in M1 cells by native murine LIF and by recombinant LIF.

FIG. 30: relates to step 3: Induction of differentiation in colonies of M1 leukaemic cells by dilutions of purified native murine LIF (o------o) and conditioned medium from yeast cells containing the YEpsec1/HLIF recombinant induced with galactose ( _ ). Medium f tom uninduced yeast cultures containing the YEpsec1/-HLIF recombinant (o_o) was inactive. Mean data from replicate 7 day cultures is presented.

Figure 31:
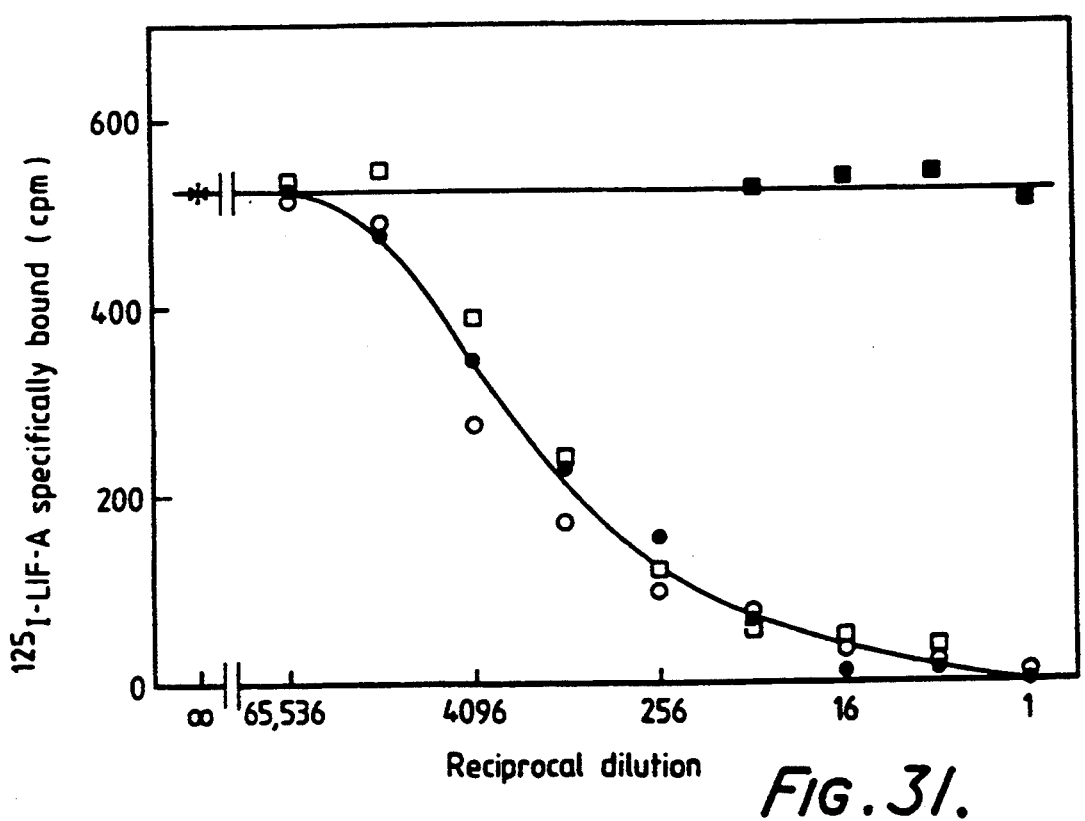
FIG. 31 shows the recombinant LIF competes with native murine LIF for binding to M1 cell receptors.

FIG. 31: relates to step 4: competition of yeast-derived HLIF with native murine $^{125}$I-LIF for binding to specific receptors on murine M1 cells. Dilutions of authentic native murine LIF-A (Example 1) (o_o), recombinant murine LIF ( _ ) and conditioned medium from yeast cells containing the YEpsec1/HLIF construct uninduced ( 13 ) and induced with galactose (□_□) were tested for ability to compete for the binding of native $^{125}$I-LIF-A to cellular receptors on murine M1 cells at 37° C., as disclosed previously.

Step 1

Modification of the Human LIF Gene for Expression in Yeast

The isolation of a recombinant DNA clone containing the human LIF gene and the nucleotide sequence of the aforementioned gene has been previously disclosed (Example 10). The nucleotide sequence of 1297 bp of DNA spanning the 2 exons encoding the mature human LIF protein is shown in FIG. 25.

Murine recombinant LIF has previously been produced in yeast cells using the yeast expression vector, YEpsec1 (Example 5). This vector provides an N-terminal leader sequence derived from the killer toxin gene of *Kluyveromyces lactis,* transcribed from a galactose-inducible hybrid GAL-CYC promoter.

In order to express the protein encoded by the human LIF gene in this vector it was necessary to modify the gene in several ways. At the 5' end of the region encoding the mature protein a cleavage site for the restriction endonuclease Bam HI was introduced to allow insertion in frame with the K. lactis leader and retain an appropriate signal peptidase cleavage site (Gly-Ser). The same modification as previously applied to the mouse cDNA (pLIF7.2b) was made here. In the middle, the 693 bp intervening sequence was removed, fusing the two exons in the same translational reading frame. At the 3' end, a second translational stop codon was introduced immediately 3' of the natural stop codon, followed by a Hind III site for insertion into YEpsec1. All of the modifications were achieved by oligonucleotide-mediated mutagenesis: the ~3 kbp Bam HI fragment spanning the LIF gene was subcloned into the plasmid pEMBL8+,(Dente, L. et al, Nucleic Acids Res. 11:1645–1655, 1983) and single-stranded DNA prepared by F1 superinfection. In vitro mutagenesis was performed as described (Nisbet, I. T. and Beilharz, M. W. Gene Anal. Techn. 2:23 29, 1985), using oligonucleotides of 39, 48 and 39 bases respectively to modify the 5' end, the middle and 3' end of the gene as outlined above (see FIG. 28). The nucleotide sequence of the modified human LIF coding region is given in FIG. 29.

Step 2

Introduction of the YEpsec1/HLIF Recombinant into Yeast Cells

S. cerevisiae strain GY1+ (leu2 ura3 ade2 trp1 cir+; from G. Cesareni, EMBL Heidelberg) was transformed by the polyethylene glycol method (Klebe, R. J. et al, Gene 25: 333–34 1, 1983). Transformants were selected and maintained on synthetic minimal medium (2% carbon source, 0.67% yeast nitrogen base (Difco) supplemented with 50 µg/ml of the required amino acids) under uracil deprivation. Recombinant HLIF was produced by either of two methods. Either (1), Ura+ transformants were grown to stationary phase in non-selective medium containing 2% galactose, and the medium assayed for LIF activity or (2), Ura+ transformants were grown to stationary phase in selective minimal medium containing 2% glucose. Cells were then washed and resuspended in the same volume of selective minimal medium containing 2% ethanol and grown for 8 hours to overcome glucose repression. Transcription of the HLIF insert was then induced by diluting the cells (1:10) into synthetic minimal medium containing 2% galactose. Aliquots of culture supernatant were removed at various times after induction, filtered through Millipore filters (0.2 µm) and assayed for LIF activity directly.

Step 3

Determination of the Biological Properties of Yeast-Derived HLIF

In view of the high degree of sequence similarity between mouse and human LIF, the activity of yeast derived human LIF on murine M1 cells was assessed. Assays for differentiation-inducing activity and leukaemia-suppressive activity of yeast conditioned medium were performed in 1 ml cultures containing 300 murine M1 cells (provided by Dr M. Hozumi, Saitama Cancer Research Centre, Japan) in Dulbecco's Modified Eagle's medium with a final concentration of 20% foetal calf serum and 0.3% agar. Material to be assayed was added in serially diluted 0.1 ml volumes to the culture dish prior to the addition of the cell suspension in agar medium. Cultures were incubated for 7 days in a fully humidified atmosphere of 10% $CO_2$ in air. Cultures were scored using a dissection microscope at ×35 magnification, scoring as differentiated any colonies with a corona of dispersed cells or composed wholly of dispersed cells. Morphological examination of colonies was performed by fixing the entire culture with 1 ml 2.5% glutaraldehyde then staining the dried cultures on microscope slides using acetylcholinesterase/Luzol Fast Blue/Haematoxylin.

Medium from galactose-induced cultures of yeast containing the human coding region in YEpsec1, but not from uninduced cultures of the same yeast cells, from cultures of non-transformed yeast, or yeast containing the vector YEpsec1 alone, was able to induce typical macrophage differentiation in cultures of M1 colonies (FIG. 30). As with murine LIF, with increasing concentrations the yeast-derived human material also progressively reduced the number and size of M1 colonies developing. Comparison with purified native murine LIF indicated that the yeast conditioned medium contained up to 50,000 Units/ml of human LIF.

Step 4

Receptor Binding Specificity of Yeast-Derived Human LIF

Purified murine LIF-A (Example 1) was iodinated as disclosed previously. M1 cells were washed and resuspended at $2.5 \times 10^6/50$ µl in Hepes-buffered RPMI medium containing 10% foetal calf serum. Cells in 50 µl aliquots were incubated with 200,000 cpm of $^{125}I$-LIF-A (10 µl in the same medium) and 10 µl of control medium or serial two-fold dilutions of unlabelled pure murine LIF-A or conditioned medium from galactose-induced or uninduced cultures of yeast transformants containing the YEpsec1/HLIF construct.

Medium conditioned by galactose-induced yeast cells containing the YEpsec1/HLIF recombinant was able to compete for the binding of native murine $^{125}I$-LIF-A to specific cellular receptors on murine M1 cells to the same extent as native and recombinant murine LIF-A, at 37° C. (FIG. 31) and at 0° C. (not shown). Medium from uninduced yeast cells and from yeast cells containing the vector YEpsec1 alone did not. Thus there appears to be a strong conservation of the receptor binding domain in murine and human LIFs, compatible with the high degree of primary amino acid sequence similarity.

Step 5

Purification, Sequencing and Iodination of Yeast-Derived Human LIF

Human LIF in medium conditioned by galactose-induced yeast cells containing the YEpsec 1/HLIF recombinant was purified using steps 2 and 4 of Example 1, except that the LIF activity binding to the DEAE-Sepharose CL-6B column and eluted with the salt gradient was pooled in step 2. Purified yeast-derived human LIF was radioiodinated by incubating 1 µg of human LIF in 50 µl of 0.2M sodium phosphate buffer, pH 7.2, with 1 mCi of Na $^{125}I$ (2.7 µl) and 5 µl of 0.2 mM ICl in 2M NaCl for 60 sec. $^{125}$ I-LIF was separated from unincorporated $^{125}I$ by passage of the reaction mixture through a column of Sephadex G-25M (Pharmacia) equilibrated in phosphate buffered (20 mM, pH 7.4) saline (0.15M) containing 0.02% Tween 20 and 0.02% sodium azide. Human $^{125}$I-LIF electrophoresed on a 8-25% gradient sodium dodecyl sulphate polyacrylamide gel as a single broad band with apparent molecular weight of 170,000. Human $^{125}$I-LIF bound specifically to murine M1 cells and bone marrow cells confirming the ability of human LIF to bind to murine LIF receptors. Purified yeast-derived human LIF (approx. 10 μg) was subjected to amino-terminal amino acid sequencing as described in Example 2 and gave a single sequence of:

Ile-Thr-Pro-Val-X-Ala . . . .

This is identical to the predicted amino acid sequence of human LIF (FIG. 26) except that the sequence begins at the fourth amino acid compared to the start of the murine sequence (see Example 2) which is:

Pro-Leu-Pro-Ile-Thr-Pro-Val-Asn-Ala . . . .

This indicates that the purified yeast-derived human LIF is missing the corresponding first three amino acids of the mouse sequence but is still biologically active and still able to bind to the murine LIF receptor. The first three amino acids thus appear to be dispensable for the biological activity of LIF.

EXAMPLE 12

The following example sets out the steps used to identify and partially purify a putative native human LIF molecule.

Figure 32:
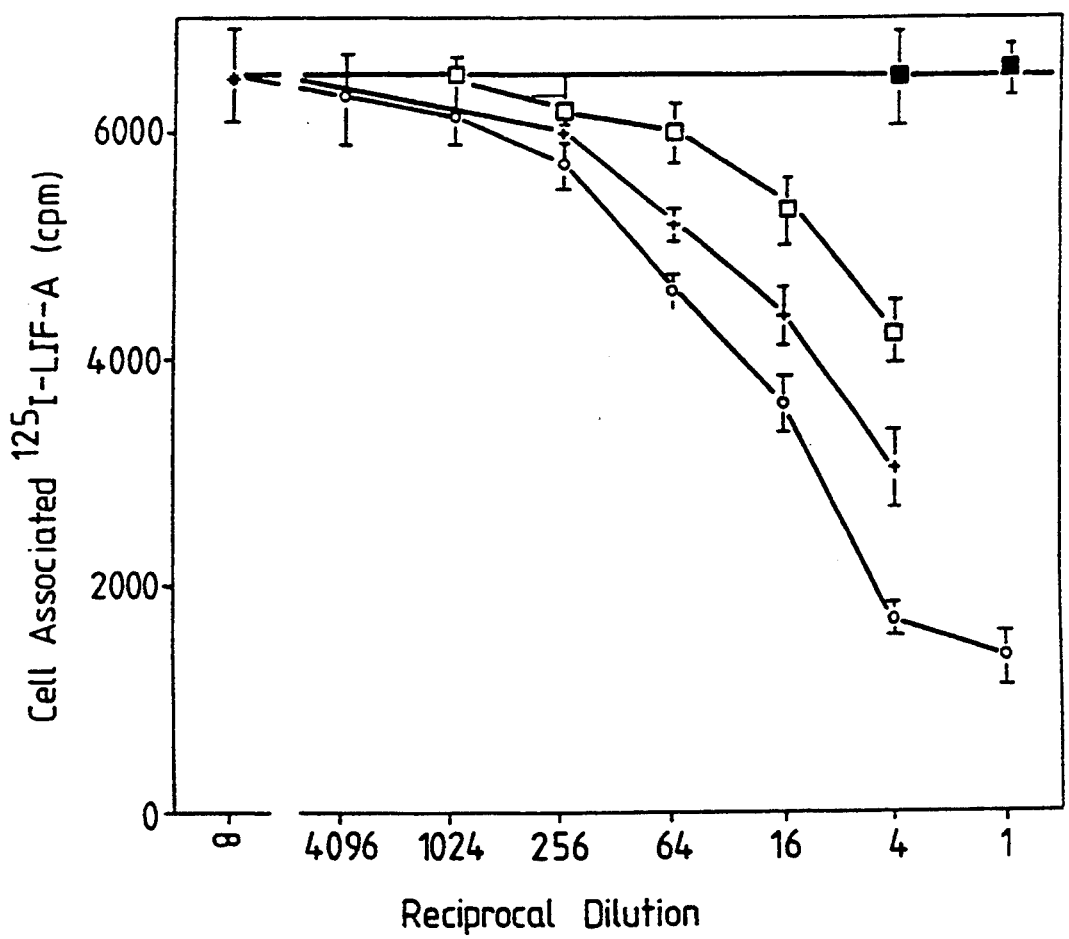
FIG. 32 shows that human bladder carcinoma conditioned media compete with nature murine LIF for cellular receptors on murine peritoneal cells.

The accompanying Figures relate to various steps of the method described below. In the Figures:

FIG. 32 relates to step 2 of the identification of a putative human LIF. FIG. 32 depicts the ability of different dilutions of medium conditioned by the human bladder carcinoma cell line 5637 (ATCC No. HTB9) [(—□—) crude or (—+—) DEAE non-binding fraction] or of native murine LIF-A (—o—) to compete for the binding of murine $^{125}$I-LIF-A to cellular receptors on murine peritoneal cells. The inability of human G-CSF (—□—) to compete for binding is also shown (undiluted=5 μg/ml).

FIG. 33: relates to step 3 of the identification of a putative human LIF: the fractionation of medium conditioned by the human bladder carcinoma cell line 5637 on a column of DEAE- Sepharose CL-6B, eluted exactly as for the previously described fractionation of murine LIF-A (Example 1), and the ability of individual fractions from this fractionation to induce the formation of differentiated colonies of murine M1 cells. Panel A shows the salt gradient, Panel B shows the fractionation of 5637 conditioned medium; Panel C shows the fractionation of Krebs II cell conditioned medium for comparison.

FIG. 34: relates to step 3 of the identification of a putative human LIF: the fractionation of medium conditioned by the human bladder carcinoma cell line 5637 on a column of lentil-lectin Sepharose 4B eluted as previously described for the fractionation of murine LIF-A (Example 1) and the ability of individual fractions from this fractionation to induce the formation of differentiated colonies of murine M1 cells. Panel A shows the gradient of α-methyl-D-mannopyrannoside, Panel B shows the fractionation of 5637 conditioned medium and Panel C shows the fractionation of Krebs II conditioned medium for Comparison.

Step 1

Medium conditioned by several human cell lines were assayed for their capacity to induce the differentiation and inhibit the proliferation of M1 murine myeloid leukaemic cells in semi-solid agar cultures (as described in Example 5, Step 4 of the present application). Several cell lines produced such an activity, of which the bladder carcinoma cell line 5637 produced the highest levels. However, the 5637 cell line has been shown previously to produce human G-CSF (Nicola, N. A. et al, *Nature* 314: 625-628, 1985; Welte, K. et al, *Proc. Natl. Acad. Sci. USA* 82: 1526-1530, 1985) which is also active in inducing differentiation of M1 cells (Tomida, M. et al, *FEBS Lett.* 207: 271-275, 1986; Neckers, L. M. and Pluznik, D. H. *Exp. Hematol.* 15: 700-703, 1987). To confirm that 5637 cells produced authentic human LIF (in addition to G-CSF), 5637-conditioned medium was further subjected to Steps 2 and 3 below.

Step 2

Medium conditioned by 5637 cells was concentrated 20-fold and tested for its ability to compete for the binding of native murine $^{125}$I-LIF-A to specific cellular receptors on murine peritoneal cells. This competition binding assay was as disclosed in Step 5 of Example 5 in the present application. 5637 cell-conditioned medium contained activity capable of competing for the binding of murine $^{125}$I-LIF-A to cellular receptors and this activity was concentrated in the DEAE non-binding fraction of 5637 CM (LIF-A) (FIG. 32). Since human and murine G-CSF do not compete, even at very high concentrations, for $^{125}$I-LIF-A binding sites, this establishes the presence in 5637-conditioned medium of a homologous human LIF activity capable of recognizing specifically the murine LIF receptor. This indicates strong conservation of the murine and human LIFs in their receptor binding domain, compatible with the high degree of primary amino acid sequence homology.

Step 3

Medium conditioned by human bladder carcinoma 5637 cells (two liters in 10% v/v foetal calf serum) was concentrated to 40 ml and chromatographed sequentially on DEAE-Sepharose CL-6B and lentil-lectin-Sepharose 4B as described previously for murine LIF from Krebs II ascites cell-conditioned medium. M1 differentiation-inducing activity from 5637 cells (putative human LIF) chromatographed in a very similar fashion to murine LIF on DEAE-Sepharose, with some activity not binding to the column (LIF-A), while the remainder bound and was eluted during the salt gradient (LIF-B) (FIG. 33). Similarly, the putative human LIF behaved like murine LIF on lentil-lectin-Sepharose chromatography with a proportion of activity binding to the column indicating the presence of mannose-containing carbohydrates on the glycoprotein (FIG. 34). Thus by its cross-reactivity in inducing murine M1 cell differentiation, its ability to recognize specifically the murine LIF cellular receptor, and its biochemical fractionation characteristics, the human activity in 5637 cell conditioned media meets the criteria of the native human analogue of murine LIF.

Native human LIF from 5637 cell conditioned medium was purified by steps 2 and 4 of Example 1, pooling the non-binding LIF activity from step 2 and the binding LIF activity from step 4. This pooled LIF activity was fractionated by reverse-phase HPLC as for step 5 of Example 1 except that a Brownlee RP300 C8 column was used twice, first using a gradient from 0–60% CH$_3$CN in 0.1% TFA and then using a gradient from 45–55% CH$_3$CN in 0.1% TFA. In the second gradient human LIF eluted at 50% CH$_3$CN and when electrophoresed on 8–25% gradient sodium dodecyl sulphate polyacrylamide gels showed a major silver staining band of apparent molecular weight 73,000. Native purified human LIF was radioiodinated as described in step 5 of Example 10 and bound specifically to murine M1 cells and mouse bone marrow cells as described for yeast-derived human $^{125}$I-LIF (step 5 of Example 11).

We claim:

1. A method of producing human leukemia inhibitory factor (LIF) comprising the steps of
   (a) transforming or transfecting suitable host cells with a recombinant DNA molecule comprising a nucleotide sequence which codes for human LIF,
   (b) culturing the host cells of step (a) under conditions in which said cells express the recombinant DNA and produce human LIF, and
   c) recovering said human LIF.

2. The method of claim 1 in which said recombinant DNA molecule codes for human LIF having the amino acid sequence set forth in FIG. 26.

3. The method of claim 1 in which said recombinant DNA molecule comprises a nucleotide sequence the complement of a DNA sequence coding for human LIF.

4. The method of claims 1, 2, or 3, wherein the recombinant DNA molecule further comprises a promoter sequence operably linked to said nucleotide sequence to allow expression of the recombinant DNA and production of human LIF by said host cells.

5. The method of claim 4, wherein said nucleotide sequence further codes for a signal sequence contiguous with the amino acid sequence of human LIF, wherein said signal sequence directs secretion of human LIF from said host cells.

6. The method according to claim 5 wherein said signal sequence is cleavable from the human LIF polypeptide such that human LIF is recoverable as a mature biologically active polypeptide.

7. The method of claim 1, wherein the host cell is selected from the group consisting of bacteria, yeast and mammalian cells.

8. The method of claim 7 wherein the host cell is *E. coli*.

9. The method of claim 7 wherein the host cell is *Saccharomyces cerevisiae*.

10. The method of claim 7 wherein the host cell is a hematopoietic cell.

11. The method of claims 9 or 10 wherein said human LIF is glycosylated.

12. A method of producing murine leukemia inhibitory factor (LIF) comprising the steps of
    (a) transforming or transfecting suitable host cells with a recombinant DNA molecule comprising a nucleotide sequence which codes for murine LIF,
    (b) culturing the host cells of step (a) under conditions in which said cells express the recombinant DNA and produce murine LIF, and
    (c) recovering said murine LIF.

13. The method of claim 12 in which said recombinant DNA molecule codes for murine LIF having the amino acid sequence set forth in FIG. 26.

14. The method of claim 12 in which said recombinant DNA molecule comprises a nucleotide sequence the complement of a DNA sequence coding for murine LIF.

15. The method of claims 12, 13 or 14, wherein the recombinant DNA molecule further comprises a promoter sequence operably linked to said nucleotide sequence to allow expression of the recombinant DNA and production of murine LIF by said host cells.

16. The method of claim 15, wherein said nucleotide sequence further codes for a signal sequence contiguous with the amino acid sequence of murine LIF, wherein said signal sequence directs secretion of murine LIF from said host cells.

17. The method according to claim 16 wherein said signal sequence is cleavable from the murine LIF polypeptide such that murine LIF is recoverable as a mature biologically active polypeptide.

18. The method of claim 12 wherein the host cell is selected from the group consisting of bacteria, yeast and mammalian cells.

19. The method of claim 18 wherein the host cell is *E. coli*.

20. The method of claim 18 wherein the host cell is *Saccharomyces cerevisiae*.

21. The method of claim 18 wherein the host cell is a hematopoietic cell.

22. The method of claims 20 or 21 wherein said murine LIF is glycosylated.

* * * * *

UNITED STATES PATENT AND TRADEMARK OFFICE
CERTIFICATE OF CORRECTION

PATENT NO. : 5,427,925
DATED : June 27, 1995
INVENTOR(S) : David P. Gearing, et al.

It is certified that error appears in the above-indentified patent and that said Letters Patent is hereby corrected as shown below:

On the Title Page, Section [54]: "RECOMBNIANT" and "LEUKEMIA INHIBITOR" should read --RECOMBINANT-- and --LEUKAEMIA INHIBITORY--

On the Title Page, Section [30], line 4: "PI14903" should read --PI4903--

On the Title Page, Section [30], line 5: "PI16005" should read --PI6005--

In the Abstract, line 2: "leukemia" should read --leukaemia--

Column 1, lines 2 & 3" "RECOMBNIANT" and "LEUKEMIA INHIBITOR" should read --RECOMBINANT-- and --LEUKAEMIA INHIBITORY--

Column 2, line 10: "turnout" should read --tumour--

Column 2, line 12: "Progenitor" should read --progenitor--

Column 2, line 28: "Cells" should read --cells--

Column 2, line 55: "clearable" should read --cleavable--

UNITED STATES PATENT AND TRADEMARK OFFICE
CERTIFICATE OF CORRECTION

PATENT NO. : 5,427,925
DATED : June 27, 1995
INVENTOR(S) : David P. Gearing, et al.

It is certified that error appears in the above-indentified patent and that said Letters Patent is hereby corrected as shown below:

Column 3, line 1: "not-to" should read --not to--
Column 5, line 22: "illustrates-the" should read --illustrates the--
Column 5, line 38: "leukemia" should read --leukaemia--
Column 7, line 14: "the-expression" should read --the expression--
Column 8, line 19: "turnout" should read --tumour--
Column 8, line 49: "mm" should read --mM--
Column 8, line 56: " =-methyl" should read -- α-methyl --
Column 9, line 18: after "injected," delete -- - --
Column 12, line 1: "Ely" should read --Gly--
Column 12, line 65: "arian" should read --avian--
Column 19, line 6: "Step 31" should read --Step 3--
Column 24, line 62: "Assays" should read --An assay--

UNITED STATES PATENT AND TRADEMARK OFFICE
CERTIFICATE OF CORRECTION

PATENT NO. : 5,427,925
DATED : June 27, 1995
INVENTOR(S) : David P. Gearing, et al.

It is certified that error appears in the above-indentified patent and that said Letters Patent is hereby corrected as shown below:

Column 24, lines 63-64: delete "both the glutathione S-transferase/LIF fusion protein and"
Column 24, line 65: "were" should read --was--
Column 24, lines 66-67: delete "Both preparations of LIF were" and insert --This LIF preparation was--
Column 24, line 68: "activities" should read --activity--
Column 26, line 13: "mm" should read --mM--
Column 28, line 12: "'Rail" should read --Raji--
Column 31, line 16: "arian" should read --avian--
Column 32, lines 38 & 46: "( ___ )" should read --(● ___ ●)--
Column 32, lines 38-39: "ftom" should read --from--
Column 32, line 48: "( 13 )" should read --(■ ___ ■)--
Column 33, line 34: "34 1" should read --341--
Column 34, line 10: "Luzol" should read --Luxol--

UNITED STATES PATENT AND TRADEMARK OFFICE
CERTIFICATE OF CORRECTION

PATENT NO. : 5,427,925
DATED : June 27, 1995
INVENTOR(S) : David P. Gearing, et al.

It is certified that error appears in the above-indentified patent and that said Letters Patent is hereby corrected as shown below:

Column 35, line 68: "Comparison" should read --comparison--

Column 37, line 16, Claim 1: "leukemia" should read --leukaemia--

Column 37, lines 30-31: "sequence the complement" should read --sequence that hybridizes to the complement--

Column 38, line 9, Claim 12: "leukemia" should read --leukaemia--

Column 38, lines 22-23, Claim 14: "sequence the complement" should read --sequence that hybridizes to the complement--

Signed and Sealed this

Twenty-fourth Day of September, 1996

Attest:

BRUCE LEHMAN

*Attesting Officer*  *Commissioner of Patents and Trademarks*